US011471520B2

(12) United States Patent
Barry et al.

(10) Patent No.: US 11,471,520 B2
(45) Date of Patent: Oct. 18, 2022

(54) **ENHANCED *SHIGELLA*-ENTEROTOXIGENIC *E. COLI* MULTI-VALENT VACCINE**

(71) Applicant: University Of Maryland, Baltimore, Baltimore, MD (US)

(72) Inventors: Eileen M. Barry, Ellicott City, MD (US); Myron M. Levine, Columbia, MD (US)

(73) Assignee: University Of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 17/042,671

(22) PCT Filed: Apr. 3, 2019

(86) PCT No.: PCT/US2019/025602
§ 371 (c)(1),
(2) Date: Sep. 28, 2020

(87) PCT Pub. No.: WO2019/195437
PCT Pub. Date: Oct. 10, 2019

(65) Prior Publication Data
US 2021/0121553 A1   Apr. 29, 2021

Related U.S. Application Data

(60) Provisional application No. 62/651,973, filed on Apr. 3, 2018.

(51) Int. Cl.
*A61K 39/112*   (2006.01)
*A61K 39/108*   (2006.01)
*A61K 39/00*    (2006.01)

(52) U.S. Cl.
CPC ...... *A61K 39/0283* (2013.01); *A61K 39/0258* (2013.01); *A61K 2039/522* (2013.01); *A61K 2039/70* (2013.01)

(58) Field of Classification Search
None
See application file for complete search history.

(56) References Cited

U.S. PATENT DOCUMENTS

2015/0026693 A1   9/2015   Savarino

FOREIGN PATENT DOCUMENTS

WO   WO2016/202872 A1   12/2016

OTHER PUBLICATIONS

Anantha RP, McVeigh AL, Lee LH, Agnew MK, Cassels FJ, Scott DA, et al. Evolutionary and functional relationships of colonization factor antigen i and other class 5 adhesive fimbriae of enterotoxigenic *Escherichia coli*. Infect Immun. 2004; 72(12):7190-201.

Blackwelder WC, Biswas K, Wu Y, Kotloff KL, Farag TH, Nasrin D, et al. Statistical Methods in the Global Enteric Multicenter Study (GEMS). Clin Infect Dis. 2012; 55 Suppl 4:S246-53. doi: 10.1093/cid/cis788.:S246-S253.

Del Canto F., Botkin DJ, Valenzuela P, Popov V, Ruiz-Perez F, Nataro JP, et al. Identification of *coli* Surface Antigen 23, a novel adhesin of enterotoxigenic *Escherichia coli*. Infect Immun. 2012; 80(8):2791-801.

Echeverria P, Seriwatana J, Taylor DN, Changchawalit S, Smyth CJ, Twohig J, et al. Plasmids coding for colonization factor antigens I and II, heat-labile enterotoxin, and heat-stable enterotoxin A2 in *Escherichia coli*. Infect Immun. 1986; 51(2):626-30.

Evans DG, Evans DJ, Jr. New surface-associated heat-labile colonization factor antigen (CFA/II) produced by enterotoxigenic *Escherichia coli* of serogroups O6 and O8. Infect Immun. 1978; 21(2):638-47.

Fleckenstein J, Sheikh A, Qadri F. Novel antigens for enterotoxigenic *Escherichia coli* vaccines. Expert Rev Vaccines. 2014; 13(5):631-9.

Gaastra W, Svennerholm AM. Colonization factors of human enterotoxigenic *Escherichia coli* (ETEC). Trends Microbiol. 1996; 4(11):444-52.

Guevara CP, Luiz WB, Sierra A, Cruz C, Qadri F, Kaushik RS, et al. Enterotoxigenic *Escherichia coli* CS21 pilus contributes to adhesion to intestinal cells and to pathogenesis under in vivo conditions. Microbiology. 2013; 159(Pt 8):1725-35.

Haines S, Gautheron S, Nasser W, Renauld-Mongenie G. Identification of Novel Components Influencing Colonization Factor Antigen I Expression in Enterotoxigenic *Escherichia coli*. PLoS One. 2015; 10(10):e0141469.

Isidean SD, Riddle MS, Savarino SJ, Porter CK. A systematic review of ETEC epidemiology focusing on colonization factor and toxin expression. Vaccine. 2011; 29(37):6167-78.

Kotloff KL, Blackwelder WC, Nasrin D, Nataro JP, Farag TH, van EA, et al. The Global Enteric Multicenter Study (GEMS) of Diarrheal Disease in Infants and Young Children in Developing Countries: Epidemiologic and Clinical Methods of the Case/Control Study. Clin Infect Dis. 2012; 55 Suppl 4:S232-45. doi: 10.1093/cid/cis753.:S232-S245.

Levine MM, Ristaino P, Marley G, Smyth C, Knutton S, Boedeker E, et al. *coli* surface antigens 1 and 3 of colonization factor antigen II-positive enterotoxigenic *Escherichia coli*: morphology, purification, and immune responses in humans. Infect Immun. 1984; 44:409-20.

Levine MM. *Escherichia coli* that cause diarrhea: enterotoxigenic, enteropathogenic, enteroinvasive, enterohemorrhagic, and enteroadherent. J Infect Dis. 1987; 155:377-89.

Levine MM, Kotloff KL, Nataro JP, Muhsen K. The Global Enteric Multicenter Study (GEMS): Impetus, Rationale, and Genesis. Clin Infect Dis. 2012; 55 Suppl 4:S215-24. doi: 10.1093/cid/cis761.:S215-S224.

(Continued)

*Primary Examiner* — Brian Gangle
(74) *Attorney, Agent, or Firm* — Wolter Van Dyke Davis, PLLC; Eugene J. Molinelli; Martha Cassidy

(57) ABSTRACT

The invention relates to a multivalent *Shigella*/Enterotoxigenic *Escherichia coli* vaccine for use in prophylaxis and treatment of diarrheal disease. The *Shigella*-ETEC vaccine provides increased coverage of a broader range of ETEC and *Shigella* isolates than prior vaccines, and includes CS14 antigens and serotypes (*S. flexneri* 7a, or *S. flexneri* 1b).

20 Claims, 3 Drawing Sheets

Specification includes a Sequence Listing.

(56) References Cited

OTHER PUBLICATIONS

Nicklasson M, Sjoling A, von MA, Qadri F, Svennerholm AM. Expression of colonization factor CS5 of enterotoxigenic *Escherichia coli* (ETEC) is enhanced in vivo and by the bile component Na glycocholate hydrate. PLoS One. 2012; 7(4):e35827.

Tacket CO, Maneval DR, Levine MM. Purification, morphology, and genetics of a new fimbrial putative colonization factor of enterotoxigenic *Escherichia coli* O159:H4. Infect Immun. 1987; 55:1063-9.

Vidal RM, Valenzuela P, Baker K, Lagos R, Esparza M, Livio S, et al. Characterization of the most prevalent colonization factor antigens present in Chilean clinical enterotoxigenic *Escherichia coli* strains using a new multiplex polymerase chain reaction. Diagn Microbiol Infect Dis. 2009; 65(3):217-23.

Wolf MK, Andrews GP, Tall BD, McConnell MM, Levine MM, Boedeker EC. Characterization of CS4 and CS6 antigenic components of PCF8775, a putative colonization factor complex from enterotoxigenic *Escherichia coli* E8775. Infect Immun. 1989; 57:164-73.

International Search Report and Written Opinion for International Patent Application No. PCT/US19/25602 dated Jul. 10, 2019, pp. 1-11.

Livio, S. et al., "Shigella Isolates From the Global Enteric Multi-center Study Inform Vaccine Development. Clinical Infectious Disease," Oct. 1, 2014, Epub Jun. 23, 2014, vol. 59, No. 7; pp. 933-941.

Al Tboum, Z. et al., "Attenuated Shigella flexneri 2a delta-guaBA Strain CVD 1204 Expressing Enterotoxigenic *Escherichia coli* (ETEC) CS2 and CS3 Fimbriae as a Live Mucosal Vaccine against Shigella and ETEC Infection," Infection and Immunity. May 2001, vol. 69. No. 5; pp. 3150-3158.

Delaine, BC., et al., "Characterization of a multicomponent live, attenuated Shigella flexneri vaccine," Pathogens and Disease. Jul. 2016, Epub Apr. 21, 2016, vol. 74, No. 5; pp. 1-12.

Sakellaris, H. et al., "A conserved residue in the tip proteins of CS1 and CFA/I pili of enterotoxigenic *Escherichia coli* that is essential for adherence," Proceedings of the National Academy of Sciences of the U.S.A. Oct. 26, 1999, vol. 96, No. 22; pp. 12828-12832.

Wei, Jet et. al., "Complete Genome Sequence and Comparative Genomics of Shigella flexneri Serotype 2a Strain 2457T," Infection and Immunity. May 2003, vol. 71, No. 5; pp. 2775-2786.

Extended European Search Report issued in corresponding EP19781096.3, dated Dec. 8, 2021.

BreOnna C. Delaine, et al.; Characterization of a multicomponent live, attenuated Shigella flexneri vaccine; FEMS Journals investing in science, Pathogens and Disease, vol. 74, No. 5, 2016, pp. 1-12.

Eileen M. Barry, et al.; "A tale of two bacterial enteropathogens and one multivalent vaccine"; Cellular Microbiology, 2019; 21:e13067, https://doi.org/10.1111/cmi.13067.

Eileen M. Barry, et al.; "Immune responses elicited against multiple enterotoxigenic *Escherichia coli* fimbriae and mutant LT expressed in attenuated Shigella vaccine strains", Elsevier; Vaccine 21 (2003) p. 333-340; www.elsevier.com/locate/vaccine.

Eileen M. Barry, et al.; "Immunogenicity of multivalent Shigella-ETEC candidate vaccine strains in a guinea pig model"; Elsevier; Vaccine 24 (2006) p. 3727-3734; www.elsevier.com/locate/vaccine.

SEQUENCE LISTING

<160> NUMBER OF SEQ ID NOS: 42

<210> SEQ ID NO 1
<211> LENGTH: 19

```
<212> TYPE: DNA
<213> ORGANISM: Artificial Sequence
<220> FEATURE:
<223> OTHER INFORMATION: Synthetic

<400> SEQUENCE: 1
gcacacggag ctcctcagt                                              19

<210> SEQ ID NO 2
<211> LENGTH: 23
<212> TYPE: DNA
<213> ORGANISM: Artificial Sequence
<220> FEATURE:
<223> OTHER INFORMATION: Synthetic

<400> SEQUENCE: 2
tccttcatcc tttcaatggc ttt                                         23

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
ttctttctgt attgtctttt tcacc                                       25

<210> SEQ ID NO 4
<211> LENGTH: 22
<212> TYPE: DNA
<213> ORGANISM: Artificial Sequence
<220> FEATURE:
<223> OTHER INFORMATION: Synthetic

<400> SEQUENCE: 4
taatagcacc cggtacaagc ag                                          22

<210> SEQ ID NO 5
<211> LENGTH: 26
<212> TYPE: DNA
<213> ORGANISM: Artificial Sequence
<220> FEATURE:
<223> OTHER INFORMATION: Synthetic

<400> SEQUENCE: 5
cctcgacata taacatgatg caactc                                      26

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
aaattgccaa cattagcttt ttca                                        24

<210> SEQ ID NO 7
<211> LENGTH: 23
<212> TYPE: DNA
<213> ORGANISM: Artificial Sequence
<220> FEATURE:
<223> OTHER INFORMATION: Synthetic

<400> SEQUENCE: 7
```

```
actattggtg caatggctct gac                                              23
```

<210> SEQ ID NO 8
<211> LENGTH: 23
<212> TYPE: DNA
<213> ORGANISM: Artificial Sequence
<220> FEATURE:
<223> OTHER INFORMATION: Synthetic

<400> SEQUENCE: 8

```
caggatccca aagtcattac aag                                              23
```

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9

```
gagaagacca ttagcgttac gg                                               22
```

<210> SEQ ID NO 10
<211> LENGTH: 23
<212> TYPE: DNA
<213> ORGANISM: Artificial Sequence
<220> FEATURE:
<223> OTHER INFORMATION: Synthetic

<400> SEQUENCE: 10

```
ccctgatatt gaccagctgt tag                                              23
```

<210> SEQ ID NO 11
<211> LENGTH: 23
<212> TYPE: DNA
<213> ORGANISM: Artificial Sequence
<220> FEATURE:
<223> OTHER INFORMATION: Synthetic

<400> SEQUENCE: 11

```
actgtaactg ctagcgttga tcc                                              23
```

<210> SEQ ID NO 12
<211> LENGTH: 23
<212> TYPE: DNA
<213> ORGANISM: Artificial Sequence
<220> FEATURE:
<223> OTHER INFORMATION: Synthetic

<400> SEQUENCE: 12

```
tgcttcctgc attaataacg agt                                              23
```

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13

```
cccactctaa ccaaagaact gg                                               22
```

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
cgtatttcca gcatttttat cca                                                23

<210> SEQ ID NO 15
<211> LENGTH: 23
<212> TYPE: DNA
<213> ORGANISM: Artificial Sequence
<220> FEATURE:
<223> OTHER INFORMATION: Synthetic

<400> SEQUENCE: 15
attgatattt tgcaagctga tgg                                                23

<210> SEQ ID NO 16
<211> LENGTH: 23
<212> TYPE: DNA
<213> ORGANISM: Artificial Sequence
<220> FEATURE:
<223> OTHER INFORMATION: Synthetic

<400> SEQUENCE: 16
gtcacatctg cggttgatag agt                                                23

<210> SEQ ID NO 17
<211> LENGTH: 18
<212> TYPE: DNA
<213> ORGANISM: Artificial Sequence
<220> FEATURE:
<223> OTHER INFORMATION: Synthetic

<400> SEQUENCE: 17
tccgctcccg ttactcag                                                      18

<210> SEQ ID NO 18
<211> LENGTH: 25
<212> TYPE: DNA
<213> ORGANISM: Artificial Sequence
<220> FEATURE:
<223> OTHER INFORMATION: Synthetic

<400> SEQUENCE: 18
gaaaagcgtt cacactgttt atatt                                              25

<210> SEQ ID NO 19
<211> LENGTH: 23
<212> TYPE: DNA
<213> ORGANISM: Artificial Sequence
<220> FEATURE:
<223> OTHER INFORMATION: Synthetic

<400> SEQUENCE: 19
aaatgtatcc caggtaacgg tct                                                23

<210> SEQ ID NO 20
<211> LENGTH: 23
<212> TYPE: DNA
<213> ORGANISM: Artificial Sequence
<220> FEATURE:
<223> OTHER INFORMATION: Synthetic

<400> SEQUENCE: 20
tgttgattag gcgtaacctc tgt                                                23

```
<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
tgctcccgtt actaaaaata c                                              21

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
tagatgtcgt atcactacgt                                                20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
gcgaataaca atgatgcaag                                                20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
cctgactggt ttacaagata                                                20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
gggactgcca caatgaattt                                                20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
cagcaccacc tgctgattta                                                20

<210> SEQ ID NO 27
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 27
tttgcaaccg acatctacca                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
ccggatgtag ttgctccaat                                               20

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
taaacttgat cttctgcaag c                                             21

<210> SEQ ID NO 30
<211> LENGTH: 21
<212> TYPE: DNA
<213> ORGANISM: Artificial Sequence
<220> FEATURE:
<223> OTHER INFORMATION: Synthetic

<400> SEQUENCE: 30
tcaggcgcag ttccttgtgt g                                             21

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
gcatgaatcg taagctgttg                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
gcatgaatcg taagctgttg                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
atccgtcagg tgtttgtggt                                               20

<210> SEQ ID NO 34
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 34
cacctgaatt cctcgacagg                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
aggtatccaa atccgcactg                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
catcagccag cacataggaa                                               20

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
tcatgagcct gctggaagtt atca                                          24

<210> SEQ ID NO 38
<211> LENGTH: 24
<212> TYPE: DNA
<213> ORGANISM: Artificial Sequence
<220> FEATURE:
<223> OTHER INFORMATION: Synthetic

<400> SEQUENCE: 38
tccggctacc taaagtaatt gagt                                          24

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
ccactttctt ccagcaacca                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
```

```
ccttggtacc attgctggtt                                            20

<210> SEQ ID NO 41
<211> LENGTH: 22
<212> TYPE: DNA
<213> ORGANISM: Artificial Sequence
<220> FEATURE:
<223> OTHER INFORMATION: Synthetic

<400> SEQUENCE: 41
gtgaaggtga agcccgtgaa gt                                         22

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
tgcagcagca ttgcggttac g                                          21
```

ENHANCED SHIGELLA-ENTEROTOXIGENIC E. COLI MULTI-VALENT VACCINE

CROSS-REFERENCE TO RELATED APPLICATIONS

This application is a 371 national stage application of PCT Application No. PCT/US19/25602, filed Apr. 3, 2019, and claims the benefit of U.S. provisional application Ser. No. 62/651,973, filed 3 Apr. 2018. The entire contents of this application is hereby incorporated by reference as if fully set forth herein.

GOVERNMENT FUNDING SUPPORT

This invention was made with government support under grant nos. AI 109776 and AI 142725, awarded by the National Institutes of Health. The government has certain rights in the invention.

REFERENCE TO SEQUENCE LISTING SUBMITTED VIA EFS-WEB

This application includes an electronically submitted sequence listing in .txt format. The .txt file contains a sequence listing entitled "15024361PC0_ST25_SequenceListing" created on May 3, 2019 and is 8 KB in size. The sequence listing contained in this .txt file is part of the specification and is hereby incorporated by reference herein in its entirety.

BACKGROUND

1. Field of the Invention

The present invention relates to the fields of medicine and in particular to a multi-component live attenuated *Shigella* vaccine which comprises additional antigens from *Shigella* serotypes and fimbrial colonization antigens from Enterotoxigenic *Escherichia coli* (ETEC). This composition produces a vaccine with enhanced and broader protection against *Shigella* and ETEC pathogens useful against diarrheal disease, including dysentery.

2. Background of the Invention

Colonization factors, including fimbriae from Enterotoxigenic *E. coli* (ETEC) are critical antigens and targets for vaccine antigens to induce antibodies that block colonization and disease. Isolates of ETEC express antigenically distinct colonization factor antigens. A vaccine with broad coverage against ETEC therefore should include multiple colonization factor antigens. The major colonization factor antigens previously recognized include CFA/I and CS1 through CS6.

Enterotoxigenic *Escherichia coli* (ETEC) cause diarrheal disease in children of less than 5 years of age in developing countries and travelers' diarrhea in persons from industrialized countries who visit developing countries, including military personnel. Clinical isolates of ETEC can produce a heat-labile enterotoxin (LT) that resembles cholera toxin and/or one or more heat-stable enterotoxins (ST) including human ST (STh) and porcine ST (STp). Strains can produce both LT and ST (LT/ST strains) or be ST-only or LT-only. Most ETEC encode colonization factors (CFs) that allow the pathogen to attach to proximal small intestine enterocytes, the critical site of host-pathogen interaction, before expressing enterotoxins that decrease villus tip cell absorption and evoke overt secretion of electrolytes and water by crypt cells.

*Shigella* and ETEC have long been recognized as important worldwide pathogens, especially in low resource settings. Recent data from the Global Enteric Multicenter Study (GEMS) identified *Shigella* and ETEC among the top 4 pathogens causing moderate to severe diarrhea (MSD) in children of less than 5 years of age. The global burden of *Shigella* was estimated to include 163 million cases and more than 74,000 deaths each year. The global burden of ETEC is estimated as >400 million cases of diarrhea annually with an estimated 120,000 deaths. More recently, these pathogens have been recognized as causes of considerable disease in the US. *Shigella* is the third most common enteric bacterial infection in the US causing about 500,000 cases (27,000 drug resistant) per year with 6,000 hospitalizations and 70 deaths. *Shigella* is easily spread from person to person because of its extremely low infectious dose and, causes infection in populations with compromised hygiene including children in daycare centers and individuals in custodial institutions. ETEC has been estimated to cause up to 10 million episodes of diarrhea each year in travelers, including military personnel. A vaccine that provides broad protection against these pathogens will be a valuable public health tool in multiple populations.

Three main families of Colonization Factor Antigens (CFAs) that cause diarrheal illness or dysentery in humans are encoded by ETEC, including CFA/I, CFA/II and CFA/IV. CFA/I is the sole member of that family. CFA/II strains encode *coli* surface (CS) antigen 3 (CS3) alone or in combination with CS1 or CS2, while CFA/IV strains encode CS6, either alone or in conjunction with CS4 or CS5. CFA/I, CS1, CS2, CS4 and CS5 are rigid fimbriae of diameter of about 6-7 nm; CS3 consists of thin flexible fibrillae 2-3 run in diameter; and CS6 morphology is nondescript.

ETEC vaccines designed to stimulate anti-CF immunity, with or without accompanying antitoxic immunity, are in clinical development. These include purified fimbrial antigens or tip adhesins, inactivated fimbriated ETEC, attenuated ETEC expressing CFs, and bacterial live vectors, such as *Shigella*, that encode ETEC CFs. Stimulating intestinal secretory IgA antibodies that bind CFs and prevent ETEC from attaching to human small intestine mucosa is generally considered to be fundamental to a successful ETEC vaccine, although some contend that parenteral vaccine-induced serum IgG antibodies that transude onto intestinal mucosa may also prevent diarrhea in humans caused by bacterial enteropathogens. Most ETEC vaccines contain CFA/I, CS1, CS2, CS3, CS5 and CS6 antigens, and some also include CS4, along with an LT toxoid.

Minor putative CFs also exist for which data supporting their role in pathogenesis in humans is less compelling or lacking, although they mediate attachment to human cells in tissue culture. Possible exceptions are CS17 LT-only strains that evoked diarrhea in challenged volunteers. Minor CF antigens CS7, CS12, CS14, CS17, CS19, CS20, CS21 and CS30 have received much attention, while others have also been described including CS8, CS10, CS11, CS13, CS15, CS18 and CS23. The only minor CF statistically associated with diarrhea in the GEMS study was CS14 (Vidal 2019). Addition of a CS14 antigen in a vaccine that includes the major colonization factors extends coverage of the vaccine. Diarrheal diseases caused by ETEC remain a serious problem in the developing world, therefore there remains in the art a need for improved vaccines with a broad coverage of ETEC.

*Shigella* is a genus of bacteria closely related to *E. coli*, and causes the diarrheal disease shigellosis in primates. It is one of the leading causes of diarrhea worldwide and is one of the top four pathogens causing moderate-to-severe diarrhea in children in Africa and South Asia. *Shigella* species are classified as follows: *S. dysenteriae* (15 serotypes), *S. flexneri* (15 serotypes), *S. boydii* (19 serotypes), and *S. sonnei* (one serotype).

*S. sonnei* and *S. flexneri* are the most important causes of disease in industrialized settings as well as in less developed regions (Livio, 2014). Protective immunity against *Shigella* is directed against the LPS O-antigen and is serotype specific. While only one serotype of *S. sonnei* is required for inclusion in a broadly protective vaccine, multiple serotypes of *S. flexneri* need to be represented. Vaccination with a mixture of just 3 serotypes, *S. flexneri* 2a, 3a and 6, which express a type- and group-specific antigen found on the other serotypes (except for 7a) has been demonstrated to provide at least partial protection against challenge with heterologous *S. flexneri* serotypes in an animal model (Noriega, 1999). These four attenuated strains have been engineered to contain mutations in guaBA and sen (and set in *S. flexneri* 2a) and shown to be safe, immunogenic and protective against homologous challenge in an animal model.

SUMMARY OF THE INVENTION

Extended analysis of serotype distribution provides strategies for improvement of coverage against circulating *Shigella* isolates. There is a need in the art to extend direct coverage by the addition of attenuated derivatives of *S. flexneri* 1b and 7a. *S. flexneri* 1b accounted for 7.5% of all *Shigella* isolates in GEMS and expresses type I antigen. The inclusion of this important serotype increases direct coverage of the vaccine and provides the Type 1 antigen to increase coverage against other Type 1 strains. *S. flexneri* 7a (formerly named 1c), accounted for 2% of all GEMS *Shigella* isolates overall and has been identified as the predominant serotype in other epidemiological studies. This serotype is included in the inventive vaccine because it has a unique O-antigen structure that does not include type- and group-specific antigens found on the other serotypes and therefore is not expected to be covered by a quadravalent vaccine. In summary, the addition of *S. flexneri* serotypes 1b and 7 increases coverage and provides cross protection.

Therefore, the present invention provides a *Shigella*-ETEC vaccine with increased coverage of a broader range of ETEC and *Shigella* isolates, including CS14 antigens and serotypes (*S. flexneri* 7a, or *S. flexneri* 1b).

Specifically, the invention relates to a vaccine composition for prophylaxis and treatment of diarrheal disease and dysentery, comprising:

a. a live attenuated *Shigella* strain selected from the group consisting of *Shigella flexneri* serotype 7a, *Shigella flexneri* serotype 1b, and both *Shigella flexneri* serotype 7a and *Shigella flexneri* serotype 1b;

b. enterotoxigenic *Escherischia coli coli* (ETEC) surface antigen CS14, wherein the ETEC CS14 is expressed in one or both or the live attenuated *Shigella* strains.

Certain embodiments of the invention relate to a vaccine as described above, further comprising one or more of:

c. a live attenuated strain of *Shigella sonnei*;

d. a live attenuated strain of *Shigella flexneri* serotype 2a;

e. a live attenuated strain of *Shigella flexneri* serotype 3a; and f. a live attenuated strain of *Shigella flexneri* serotype 6.

Certain embodiments of the invention relate to a vaccine as described above, further comprising:

c. a live attenuated strain of *Shigella sonnei*;

d. a live attenuated strain of *Shigella flexneri* serotype 2a;

e. a live attenuated strain of *Shigella flexneri* serotype 3a;

f. a live attenuated strain of *Shigella flexneri* serotype 6; and g. optionally, an attenuated strain of *Shigella dysenteriae*.

Additional embodiments of the invention include a vaccine as described above, wherein one or more of the live attenuated *Shigella flexneri* strains is engineered to express one or more enterotoxigenic *Escherichia coli* (ETEC) antigens. Examples of ETEC antigens include, but are not limited to *coli* surface antigens (CS)1, CS2, CS3, CS4, CS5, CS6, CS14, Colonization Factor Antigen 1 (CFA/1), eltA2eltB (LTB), a tip adhesin, and Shiga toxin B (StxB).

Embodiments of the invention also include vaccine compositions as described above, which further comprise a pharmaceutically acceptable carrier.

In addition, some embodiments relate a vaccine composition as described above, wherein the *Shigella* strains contain mutations in guaBA and sen.

An embodiment of the invention relates to a vaccine composition as described herein, comprising:

a. live attenuated *S. sonnei*, strain CVD 1233S, which expresses ETEC antigens CS2 and CS3;

b. live attenuated *S. flexneri* serotype 2a, strain CVD 1208S, which expresses ETEC antigens CFA/L and LA2 TB;

c. live attenuated *S. flexneri* serotype 3a, strain CVD 1213, which expresses ETEC antigens CS1 and CS5;

d. live attenuated *S. flexneri* serotype 6, strain CVD 1215, which expresses ETEC antigens CS4 and CS6;

e. live attenuated *S. flexneri* serotype 1b, strain CVD 1224, which expresses ETEC antigens CS14;

f. live attenuated *S. flexneri* serotype 7a, strain CVD 1242, which expresses one or more ETEC tip adhesin antigens; and g. optionally, live attenuated *S. dysenteriae*, strain CVD 1254, which expresses ETEC antigens CFA/1 and LTB;

In other embodiments, the invention provides a method of vaccinating a subject in need thereof against diarrheal disease, comprising administering a vaccine composition as described above to the subject. Preferably, resides in an area where diarrheal disease is endemic and/or is a child of less than 5 years old.

DETAILED DESCRIPTION

1. Definitions

Figure 1:
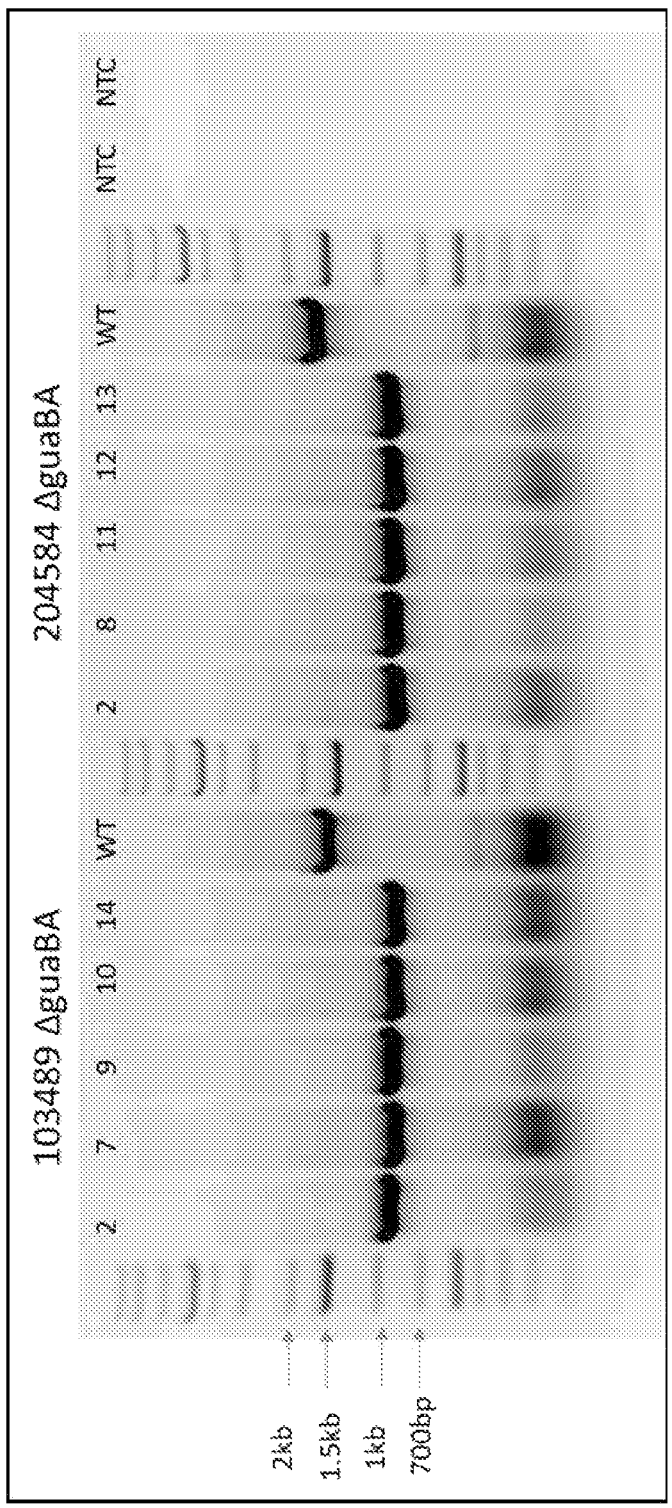
FIG. 1 is a blot showing the amplification of the guaBA locus by PCR confirming the deletion in two isolates of *S. flexneri* 1b.

Unless defined otherwise, all technical and scientific terms used herein have the same meaning as commonly understood by one of ordinary skill in the art. Although various methods and materials similar or equivalent to those described herein can be used in the practice or testing of the present invention, suitable methods and materials are described below. However, the skilled artisan understands that the methods and materials used and described are examples and may not be the only ones suitable for use in the invention. Moreover, as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary.

As used herein, the term "about" means plus or minus 20 percent of the recited value, so that, for example, "about 0.125" means 0.125±0.025, and "about 1.0" means 1.0±0.2.

As used herein, the term "prophylaxis," in the context of a disease, which includes reducing the severity of a disease, reducing the chance of contracting a disease, and a complete or partial prevention of the disease or its signs and symptoms.

As used herein, the term "treating" and its cognates refers to taking steps to obtain beneficial or desired results, including clinical results, including mitigating, alleviating or ameliorating one or more symptoms of a disease; diminishing the extent of disease; delaying or slowing disease progression; ameliorating and palliating or stabilizing a metric (statistic) of disease. The effect may be prophylactic in terms of completely or partially preventing a conditions or disease or symptom thereof and/or may be therapeutic in terms of a partial or complete cure for a condition or disease and/or adverse effect attributable to the condition or disease. "Treatment" refers to the steps taken. It can include any treatment of a condition or disease in a mammal, particularly in a human, and includes: (a) preventing the condition or disease or symptom thereof from occurring in a subject which may be predisposed to the condition or disease but has not yet been diagnosed as having it; (b) inhibiting the condition or disease or symptom thereof, such as, arresting its development; and (c) relieving, alleviating or ameliorating the condition or disease or symptom thereof, such as, for example causing regression of the condition or disease or symptom thereof.

As used herein, the term "prophylaxis" and its cognates refers to taking steps to obtain beneficial or desired results, including clinical results, and including steps to obtain total or partial prevention of a disease or condition. Vaccination for prophylaxis generally refers to administration of the composition in order to completely or partially prevent, reduce the symptoms of, severity of or duration of the illness, including partially or completely inhibiting the condition, or ameliorating the condition or progression of the condition. Prophylaxis includes reducing the bacterial infection (bacterial titer), reducing reactions to bacterial toxins associated with the disease or condition, including their symptoms, and reducing the severity or duration of symptoms.

As used herein, the term "subject" refers to any animal, preferably a mammal, and most preferably a human. Laboratory animals are included in this definition.

As used herein, the term "subject in need" refers to a subject, including a human patient, who suffers from a diarrheal disease (including dysentery) or is in an environment which might expose the subject to a diarrheal disease. For example, such a subject in need includes, but is not limited to a person of age 0 (newborn) to age 10 residing in an area where diarrheal disease is endemic or a person living in an industrialized country in a higher risk setting such as day care center or custodial institution, or a person living in an industrialized country (including military personnel) who travels to a less developed region where *Shigella* and/or ETEC are endemic.

As used herein, the terms "diarrhea," "diarrheal disease," or "dysentery" refer to an episode of three or more loose bowel movements or any number of loose stools containing blood in a 24-hour period, caused by bacterial infection.

As used herein, the term "therapeutically effective amount" refers to an amount of a therapeutic agent, which, when administered to a subject, has the intended therapeutic effect. A therapeutic effect is an effect that treats the intended disorder or condition, including improving the disease, disorder or condition, or a symptom thereof, including reduction of a symptom or delaying the onset or reoccurrence of the disease, disorder, condition, or symptom. The full therapeutic effect does not necessarily occur by administration of one dose and may occur only after administration of a series of doses. Thus, a therapeutically effective amount may be administered in one or more administrations. In the context of a vaccine, a therapeutically effective amount is an amount that reduces the chance of occurrence or reduces the severity of a disease or condition in a subject currently not suffering from the disease or condition; or an amount that produces an immune response to an etiologic agent that is associated with protection against the disease or condition. When administered to a subject currently suffering from the disease or condition, a therapeutically effective amount is an amount that induces an immune response to an etiologic agent that is associated with protection against the disease or condition and ameliorates the disease or condition in the subject.

As used herein, the term "CF" refers to colonization factor, the most common of which include CFA/I.

As used herein, the term "CS" refers to *coli* surface antigen, a group of antigens from ETEC.

As used herein, the term "CFA" refers to colonization factor antigen, which is found in ETEC isolates. CFA/I, CFA/II, and CFA/IV refer to specific colonization factor antigens I, II, and IV.

As used herein, the term "ST" refers to heat stable enterotoxins, a group of peptide toxins produced by bacterial strains such as ETEC.

As used herein, the term "LT" refers to heat labile enterotoxins, a group of toxins (inactivated at high temperatures) that are found in *E. coli*. LTA2B refers to a construct composed of the A2 subunit of LT plus the B subunit.

As used herein, the term "ETEC" refers to enterotoxigenic *Escherichia coli*, a group of *E. coli* that produce special toxins that stimulate the lining of the intestine, causing them to secrete excessive fluid, leading to diarrhea.

As used herein, the term "ETEC tip adhesin antigen" refers to antigens from tip adhesins of ETEC. Adhesins are a type of virulence factor that facilitates adhesion of the pathogen, as step in pathogenesis.

As used herein, the term "StxB" refers to the *E. coli* toxin, Shiga toxin B subunit.

2. Overview

Decades of literature, including field trials and volunteer challenge studies support the protective efficacy of live attenuated vaccines, which present the entire antigenic repertoire of the pathogen and which are delivered via the most immunologically relevant, oral route. Clinical trials demonstrated that mutations in the guaBA operon, that render *Shigella* unable to synthesize guanine nucleotides de novo, resulted in vaccine strains that were safe and immunogenic in volunteers. Additional mutations in the set and sen genes, encoding *Shigella* enterotoxins, can extend the attenuation of the vaccine strain, CVD 1208S. This attenuating strategy to additional *Shigella* component strains is used here to form a multivalent vaccine which confers broad protection. Thus, a multivalent formulation composed of 6 live attenuated strains of *Shigella* expressing ETEC colonization factor antigens and antigens to induce toxin neutralizing antibodies against heat labile (LT) and heat stable (ST) toxins is being developed.

Strategies for improvement of coverage against circulating *Shigella* isolates were developed here in order to extend direct coverage by the addition of attenuated derivatives of *S. flexneri* 1b and 7a. *S. flexneri* 1b accounted for 7.5% of all *Shigella* isolates in GEMS and expresses type I antigen. The inclusion of this important serotype increases direct coverage of the vaccine. *S. flexneri* 7a (formerly named 1c), accounted for 2% of all GEMS *Shigella* isolates overall and has been identified as the predominant serotype in other epidemiological studies. This serotype was included in the inventive vaccine because it has a unique O-antigen structure that does not include type- and group-specific antigens found on the other serotypes and therefore is not expected to be covered by any previous vaccine.

A live attenuated derivative of *S. flexneri* 1b was developed. The vaccine derivative of *S. flexneri* contains a deletion in the guaBA operon that is auxotrophic for guanine, and is defective in intracellular replication, attenuated for virulence in guinea pigs and immunogenic following immunization in guinea pigs (100% immunized animals exhibited a 2-7 fold rise in serum anti-*S. flexneri* 1b IgG following a single immunizing dose). In some embodiments, a deletion in set and/or sen can be added to this strain to enhance safety.

ETEC attach to the lining of the human small intestine by means of protein colonization factors (CFs), after which bacterial toxins stimulate intestinal secretion resulting in diarrhea. CFs from ETEC are critical antigens and targets for vaccine antigens to induce antibodies that block colonization and disease. Isolates of ETEC express antigenically distinct fimbrial types. A vaccine with broad coverage against ETEC therefore should include multiple fimbrial types. The major fimbrial antigens previously recognized include CFA/I and CS1 through CS6. Minor putative CFs also exist for which data supporting their role in pathogenesis in humans is less compelling or lacking, although they mediate attachment to human cells in tissue culture. The only minor CF statistically associated with diarrhea in the GEMS study was CS14 (Vidal 2019). Addition of a CS14 antigen in a vaccine that includes the major colonization factors extends coverage of the vaccine.

In some embodiments, the invention provides a vaccine with broad protection against a high percentage of ETEC isolates by including a minor CF (CS14) to induce antibodies against CS14. In some embodiments, this is a live attenuated *Shigella* strain (e.g., CVD 1208S) expressing CS14. In some embodiments, CVD 1208S::CS14 is engineered by insertion of an operon encoding CS14 into the chromosome of a *Shigella* strain (e.g., CVD 1208S). Immunization of guinea pigs with CVD 1208S::CS14 induced antibodies that recognize CS14. In some embodiments, the vaccine produces mucosal SIgA *Shigella* anti-O and ETEC anti-CF and anti-LT antibodies.

4. Embodiments of the Invention

Epidemiological data from the GEMS study revealed that a previously under-recognized minor fimbrial antigen from ETEC, CS14, was prevalent in isolates from children with moderate-to-severe diarrhea (MSD). Importantly, this was the only minor fimbrial antigen that was significantly associated with MSD. Inclusion of this fimbrial antigen in the instant invention vaccine would broaden the coverage of ETEC isolates.

The *Shigella* vaccine strategy of the present invention includes using a combination of a live attenuated strain of *Shigella* that represents the most prevalent species and serotypes found in clinical isolates. The vaccine includes *S. sonnei* (1 serotype) and *S. flexneri* serotypes 2a, 3a, and 6. These three *S. flexneri* serotypes were identified as expressing each of the type- and group-specific antigens found on the other 16 *flexneri* serotypes. Animal data supports cross protection between these serotypes. Two additional *S. flexneri* serotypes, 7a (previously referred to as serotype Ice) and 1b, were identified as among the most prevalent in the GEMS study. *S. flexneri* 7a has a unique O-antigen that does not express type- and group-specific antigens found on the other serotypes. Including a live attenuated derivative of *S. flexneri* 7a in the vaccine also broadens the overall coverage against *Shigella* isolates. Additionally, *S. flexneri* serotype 1b also would broaden protection since this serotype was found on 7.5% of *Shigella* isolates in the GEMS.

The genes encoding ETEC fimbrial antigen CS14 have been cloned from wild type ETEC strain into an expression plasmid. Using AttTn7 methodology developed by McKenzie and Craig for *E. coli*, the operon encoding CS14 was inserted in a permissive site on the chromosome of *Shigella* vaccine strain CVD 1208S forming CVD 1208S::CS14. Immunization of guinea pigs with CVD 1208S::CS14 induced antibodies that recognize CS14. Alternatively, the fimbrial tip adhesin of CS14, CsuD, can be expressed on the surface of *Shigella* live vectors to induce responses against this subunit which is responsible for host cell binding. The gene encoding the tip adhesin, csuD was engineered in tandem with the structural subunit gene, csuA2 on a plasmid. The plasmid directed expression of the CS14 tip adhesin in *Shigella* vaccine strain CVD 1208S. Immunization of guinea pigs with CVD 1208S (pCsuA2D) induced antibodies that recognized CS14. Purified tip proteins delivered parenterally can be used.

Analysis of the distribution of *Shigella* serotypes associated with diarrhea from the GEMS study identified *S. flexneri* 1b and 7a as serotypes that would increase the coverage of our multivalent *Shigella* vaccine. The new live attenuated *Shigella flexneri* strain of serotype 1b was engineered using selected strains (103489 and 204584) from the GEMS collection with antibiotic susceptibility. Deletions into the guaBA and sen genes were introduced using lambda red recombination (FIG. 1). The two derivatives were shown to be auxotrophic for guanine (FIG. 2), defective in intracellular replication (FIG. 3), attenuated for virulence in guinea pigs and immunogenic following immunization in guinea pigs (Table 1).

TABLE 1

Antibody Responses in Guinea Pigs Following Dose of Live Attenuated *S. flexneri* 1b Vaccine.

| Vaccine Strain | Animal Number | Fold Rise in Serum Anti-*S. flexneri* 1b LPS over Pre-immune Titer |
| --- | --- | --- |
| *S. flexneri* 1b 103849ΔguaBA | A1 | 4.5 |
| *S. flexneri* 1b 204584ΔguaBA | B3 | 2.5 |
| *S. flexneri* 1b 204584ΔguaBA | B4 | 7.3 |

The new live attenuated *Shigella flexneri* strains of serotype 1b and 7a can be engineered using selected strains from the GEMS collection with antibiotic susceptibility. Deletions into the guaBA and sen genes would be introduced. Including *S. flexneri* 1b and 7a increases direct *Shigella* coverage in the combined vaccine. The entire CS14 encoding operon can be used to express full length fimbriae. In the alternative, for the tip adhesin expression system, the gene, csuD, encoding the tip subunit only, can be used. Individual strains can be lyophilized, combined into a single combined formulation into a sachet and resuspended in buffer prior to oral delivery (as for CVD 103HgR, VAXCHORA™). See Table 2, below, for a summary of the overall formulation for a selected multivalent vaccine.

TABLE 2

Multivalent *Shigella*-ETEC Vaccine.

| *Shigella* | Vaccine, Strain | ETEC Antigen(s) Expressed |
|---|---|---|
| *S. sonnei* | CVD 1233S | CS2, CS3 |
| *S. flexneri* 2a | CVD 1208S | CFA/1, LTB |
| *S. flexneri* 3a | CVD 1213 | CS1, CS5 |
| *S. flexneri* 6 | CVD 1215 | CS4, CS6 |
| *S. flexneri* 1b | CVD 1224 | CS14 |
| *S. flexneri* 7a | CVD 1242 | Tip adhesins |
| *S. dysenteriae* | CVD 1254 | StxB |

A multivalent *Shigella*-ETEC vaccine of the invention includes 6 live attenuated strains of *Shigella* (top six lines of Table 2) expressing a total of at least 8 CFs plus LTA2B, and optionally also a live attenuated *S. dysenteriae* strain expressing StxB. Table 2 shows an example of how the combinations of *Shigella* vaccine strains and ETEC antigens can be distributed according to embodiments of the invention. However, any live attenuated *Shigella* strain can be used to express any of the combinations of CFs shown. Any live attenuated *Shigella* vaccine also can be used to express a single CF.

Another approach to broaden coverage of an ETEC vaccine is based on formulating a mix of fimbrial tip adhesin proteins. Fimbrial CFs can be classified based on the amino acid sequence relatedness of their tip adhesin proteins with several important ETEC CFs falling into Class 5 fimbriae assembled by the alternate chaperone pathway. Whereas the major fimbrial subunit proteins that create the stalks of these fimbriae differ substantially from one another antigenically, their tip adhesin proteins are highly conserved into three sub-classes. Antibody against one adhesin of the subclass cross protects against attachment by other members. Thus, protection may also be broadened by this strategy. Selecting which tip adhesins to include in a multivalent vaccine requires knowing the frequency of the CFs among ETEC globally; so GEMS data inform this vaccine strategy as well. Another strategy to broaden ETEC vaccine coverage is to include non-fimbrial surface antigens, e.g., EtpA and EatA.

Analyzing the array of CFs among GEMS ETEC isolates has provided important information to guide ETEC vaccine development and future deployment. Since ST-only and LT/ST strains are strongly incriminated as the key ETEC pathogens, a fimbrial-based ETEC vaccine that included CFA/I, CS1-6 and CS14 can confer increased protection.

Vaccines

The vaccines of the invention are designed to prevent and ameliorate diarrheal disease and dysentery by immunizing a subject in need for a group of antigens associated with these diarrheal diseases. The vaccines according to this invention contain a live attenuated strain of *Shigella flexneri* serotype 7a; a live attenuated strain of *Shigella flexneri* serotype 1b; and enterotoxigenic *Escherischia coli* surface antigen CS14, which is expressed in one or more of the *Shigella* strains. Preferably, the vaccine is a multivalent composition that provides broad coverage for the important antigens involved in diarrheal diseases caused by *Shigella* and *E. coli*.

Advantageously, the vaccines are at least pentavalent or hexavalent, combining a mixture of 5-6 *Shigella* strains, one or more of which preferably express an antigen from ETEC. For example, *S. sonnei*, *S. flexneri* strain 2a, *S. flexneri* strain 3a, *S. flexneri* strain 6, *S. flexneri* strain 1b, and *S. flexneri* strain 7a are mixed together. The vaccine most preferably contains at least *S. flexneri* strain 1b, and *S. flexneri* strain 7a, and also contains *S. flexneri* strain 2a, *S. flexneri* strain 3a, and *S. flexneri* strain 6. Preferably, the vaccines provide broad coverage for the *Shigella* antigens and the common serotypes that are shown to be important in immunity to diarrheal disease. According to certain embodiments, vaccines according to the invention can be produced with two, three, four, or five *Shigella* species, one or more of which express one or more ETEC antigens. In another embodiment, the vaccine also contains a live attenuated strain of *S. dysenteriae*. In addition, the vaccine preferably contains enterotoxigenic *Escherichia coli* (ETEC) antigens, which are expressed by one or more of the *Shigella* strains.

The *Shigella* strains CVD 1233S, CVD 1208S, CVD 1213, CVD 1215, CVD 1224, CVD 1242, and CVD 1245 are made and stored at the Center for Vaccine Development at the University of Maryland. See Tables 1 and 2. Other strains may be available to the person of skill in the art.

The ETEC antigens can be expressed in one or more of the *Shigella* strains in the multi-valent vaccine or in all of them. The ETEC antigens useful for the vaccine compositions are selected from one or more of the group consisting of *Coli* Surface (CS)1, CS2, CS3, CS4, CS5, CS6, CS14, Colonization Factor Antigen 1 (CFA/1), eltB (LTB), a tip adhesin, and Shiga toxin B (StxB). Any, or preferably all, of these antigens are expressed in at least one of the *Shigella* strains in the vaccine composition. In particular, CS14 is present in the vaccine, and CFA/I, CS1, CS2, CS3, CD5 and CD6 also are present. Although Table 2 indicates particular ETEC antigens expressed in a particular *Shigella* strain for convenience, the person of skill is aware that any of the *Shigella* strains used can be engineered according to known methods to express any of the ETEC antigens, as convenient, so the indicated antigens can be expressed in a different strain. Methods for engineering the strains to express a desired ETEC antigen are known in the art and can be found, for example in Wu et al., Infect. Immun. 79(12): 4912-4922, 2011 PMC3232646.

The vaccines are live attenuated strains of *Shigella*, and therefore preferably have been modified so that virulence is reduced in the human host, while remaining viable (live). Attenuation can be performed by any of the methods known in the art and available to persons of skill. Such methods are described in Wu et al., Infect. Immun. 79(12):4912-4922, 2011 PMC3232646 and Delaine et al., Pathog. Dis. 74(5), 2016 PMC5985478. Additionally, the bacterial strains in the vaccine compositions of the invention can contain other modifications or mutations to reduce virulence. In some embodiments, strains of *Shigella* are attenuated by mutations in guaBA and sen and/or set. In an alternative embodiment, the *Shigella* strains can be inactivated (killed) rather than attenuated, or both attenuated and inactivated so that the vaccine comprises a single strain or a mixture of killed strains. This also can be accomplished by any of the methods available in the art, such as heat inactivation, formalin treatment, and the like.

A certain embodiment of the vaccine compositions of the invention comprises live attenuated *S. sonnei*, strain CVD 1233S, which expresses ETEC antigens CS2 and CS3; live attenuated *S. flexneri* serotype 2a, strain CVD 1208S, which expresses ETEC antigens CFA/1 and LTB; live attenuated *S. flexneri* serotype 3a, strain CVD 1213, which expresses ETEC antigens CS1 and CS5; live attenuated *S. flexneri* serotype 6, strain CVD 1215, which expresses ETEC antigens CS4 and CS6; live attenuated *S. flexneri* serotype 1b, strain CVD 1224, which expresses ETEC antigens CS14; live attenuated *S. flexneri* serotype 7a, strain CVD 1242, which expresses one or more ETEC tip adhesin antigens; and optionally, live attenuated *S. dysenteriae*, strain CVD 1254, which expresses ETEC antigens CFA/1 and LTB.

Vaccine Compositions

In certain embodiments of the invention, the vaccine compositions discussed herein are formulated and administered as a pharmaceutical composition that contains the vaccine and a pharmaceutically acceptable carrier, and optionally one or more additional active agents. Preferably, the pharmaceutical compositions comprise a therapeutically effective amount of vaccine. A pharmaceutically acceptable carrier refers to any convenient compound or group of compounds that is not toxic and that does not destroy or significantly diminish the pharmacological or immunological (vaccine) activity of the agent with which it is formulated. Such pharmaceutically acceptable carriers or vehicles encompass any of the standard pharmaceutically accepted solid, liquid, or gaseous carriers known in the art, such as those discussed in the art.

A suitable carrier depends on the route of administration contemplated for the pharmaceutical composition. Routes of administration are determined by the person of skill according to convenience, the health and condition of the subject to be treated, and the location and stage of the condition to be treated. Such routes can be any route which the practitioner deems to be most effective or convenient using considerations such as the patient, the patient's general condition, and the specific condition to be treated. The live attenuated vaccines of the invention preferably are administered or delivered by the oral route. Alternatively, the strains can be inactivated, using formalin, heat, or some other agent.

In some embodiments, an inactivated multivalent *Shigella*-ETEC vaccine would be administered by the oral route or intradermal, subcutaneous, sublingual, nasal, or intramuscular routes. Other routes of administration can include, but are not limited to local or parenteral, including: oral, intravenous, intra-arterial, intrathecal, subcutaneous, intradermal, intraperitoneal, intramuscular, or local injection; rectal or vaginal suppository, topical, nasal, buccal, transdermal, sublingual, inhalation, transmucosal, wound covering, and the like. The administration can be given by transfusion or infusion, and can be administered by an implant, an implanted pump, or an external pump, or any device known in the art. Preferably, the vaccines of the present invention are administered orally, by intramuscular injection or by nasal administration. Oral administration of the vaccine is an advantageous route of administration because it is non-invasive, needing no needle and syringe, or special equipment.

Therefore, the forms which the pharmaceutical composition can take will include any form suitable or convenient for any of those routes of administration. Such product forms or dosage forms of the vaccine compositions include, but are not limited to: powders or granules for dilution, pre-filled syringes, liquids for injection, suspensions for injection, oral solutions, oral suspensions, oral emulsions, nasal spray solutions, tablets, capsules, caplets, lozenges, dragees, pills, granules, powders for inhalation, vapors, gases, rectal suppositories, vaginal suppositories, creams, lotions, oils, ointments, suspensions, emulsions, lipid vesicles, and the like. Preferably, each dosage form contains an effective amount of vaccine.

Any pharmaceutically acceptable carrier and/or excipient known in the art is contemplated for use with the invention. Carriers can include, for example, solvents, diluents, other carriers, and the like to contain the active ingredient(s) in solid, liquid, or gas form. Common carriers in solid form include starch (e.g., corn starch, potato starch, rice starch), celluloses (e.g., microcrystalline cellulose, methylcellulose, and the like), sugars (e.g., lactose, sucrose, glucose, fructose, and the like), clays, minerals (e.g., talc, and the like), gums, waxes, and the like. Common carriers in liquid of semi-liquid form include gels, lipids (e.g., lipid vesicles or nanoparticles), oils, polyethylene glycols, glycerine, propylene glycol, emulsifiers, organic solvents (e.g., ethanol), aqueous solvents (e.g., water, saline solutions, electrolyte solutions, lactated saline solutions), suspending agents, and the like.

Excipients also can include adjuvants, flavorings, preservatives, colorings, taste-masking agents, sweeteners, wetting agents, fillers, dispersants, anti-caking agents, binders, pH adjusters and buffers, lubricants (e.g., magnesium stearate and the like), antibacterial agents (e.g., benzyl alcohol, methyl parabens, and the like), antioxidants (e.g., ascorbic acid, sodium bisulfite, and the like), chelating agents (e.g., EDTA and the like), glidants (e.g., colloidal silicon dioxide), The compounds or pharmaceutical compositions containing the compounds can be provided in containers such as sachets, envelopes, blister packs, boxes, ampoules, vials, bottles, pre-filled syringes, bags, sprayers, inhalers, and the like.

Extended and sustained release compositions also are contemplated for use with and in the inventive embodiments. Thus, suitable carriers can include any of the ingredients known to achieve a delayed release, extended release or sustained release of the active components.

The vaccines of the invention, in certain embodiments, are formulated as a lyophilized vaccine powder (representing a dry mix of the six individual lyophilized vaccines strains), presented in a sachet that represents one dose of vaccine, and optionally packaged with a sachet or other package of buffer powder. In some cases, the vaccine can be provided in 5-dose, or 10-dose packages. In certain formulations of the vaccines, the dose is prepared for oral administration, by suspending the contents of the sachet in water, for example about 100 mL of water, optionally with buffer powder contained in an accompanying sachet. Once reconstituted, the resulting "cocktail" of vaccine strains in buffer solution is delivered orally. Optionally, the sachet containing the vaccine contains suitable buffers so that reconstitution is performed with water alone, or the sachet is reconstituted in a buffer solution.

This embodiment of vaccine is suitable for a travelers' vaccine, for distribution to at-risk populations and for distribution in the developing world or to military personnel. Different embodiments of the dosage forms include, but are not limited to an individual (single use) dose containing the mix of strains and a multi-pack of individual doses containing the mix of strains. Either embodiment can optionally be accompanied by a sachet of buffer powder or a buffer solution. An additional embodiment includes a multi-dose package of individual dosage sachets, such as a 5-dose or a 10-dose presentation.

Doses and Regimens

Treatment regimens include a single administration of the vaccine or a course of an initial administration and one or more "booster" administrations. Preferably, the administrations are determined by medical personnel. The initial administration is given to the subject prior to exposure to conditions where diarrheal diseases are endemic, but may be give after exposure, or after symptoms of diarrhea occur. Booster administrations are given when needed. For example, for travelers or military personnel who are entering an area where dysentery is endemic can take orally two doses ten days apart, advantageously prior to entering the area. Infants in low-to-middle income countries (LMIC) are recommended to take 1 dose at each of 10 weeks, 14 weeks, and 9 months of age. Children can be administered a booster dose at school entry (age 5-6 years), at adolescence, and then later at about age 65 years. A dose of vaccine contains about $10^8$ colony forming units (CFU) to about $5 \times 10^{10}$ CFU dry attenuated bacteria, or as recommended by medical personnel. Doses may vary from about $10^7$ CFU to about $10^{11}$ CFU, preferably about $10^8$ CFU to about $5 \times 10^{10}$ CFU, or about $5 \times 10^8$ CFU to about $10^{10}$ CFU or about $10^8$ CFU to about $10^9$ CFU, or any dose suitable as determined by the practitioner, depending on the size, exposure, general health, age, or other factors.

Subjects

The vaccine compositions according to the invention can be given to any subject, preferably a primate such as a human, in need. Subjects can include human patients, including children of any age from newborn infant to 18 years (preferably children of less than 5 years old) and adults of any age, including the elderly. Preferably, the subject is in need of vaccination against diarrheal disease. Such a subject in need therefore includes any person from 0 months or less than one month old to the extreme elderly over 100 years old. A use of the vaccines according to embodiments of the invention is administration of the vaccine in mixed populations including young infants and children. However multiple populations, or any subject in need of a broad spectrum mucosal vaccine against the epidemiologically most important *Shigella* serotypes and toxin and colonization factor types of *E. coli* (ETEC), can be served by administration of the vaccine. Multiple populations for administration of the vaccine preferably include, but are not limited to: (1) adult and child travelers who visit less developed countries where these infections are hyperendemic; (2) children and adults in certain high risk populations in developed countries; (3) children aged less than 5 years in developing countries, and (4) for mass immunization of the population to control natural or deliberate outbreaks.

In summary, embodiments of the vaccine product preferably comprise 6 live, attenuated strains of *Shigella* each expressing protective antigens from ETEC. This vaccine is intended to prevent diarrhea and dysentery caused by *S. flexneri*, *S. sonnei*, and ETEC. A component to protect against *S. dysenteriae* 1 optionally can be added if this strain becomes a public health problem.

5. Examples

This invention is not limited to the particular processes, compositions, or methodologies described, as these may vary. The terminology used in the description is for the purpose of describing the particular versions or embodiments only, and is not intended to limit the scope of the present invention which will be limited only by the appended claims. Any methods and materials similar or equivalent to those described herein can be used in the practice or testing of embodiments of the present invention. All publications mentioned herein, are incorporated by reference in their entirety; nothing herein is to be construed as an admission that the invention is not entitled to antedate such disclosure by virtue of prior invention.

Example 1. General Methods

Study Design and Population.

The rationale, assumptions, clinical, epidemiological and microbiological methods of GEMS, a 3-year case-control study undertaken among children less than 5 years of age in Gambia (Basse), Mali (Bamako), Mozambique (Manhiga) and Kenya (Siaya County) in sub-Saharan Africa and India (Kolkata), Bangladesh (Mirzapur) and Pakistan (Karachi-Bin Qasim Town) in South Asia, have been described. MSD was defined as an acute episode of diarrhea (3 or more loose stools during a 24-hour period) that started within the previous 7 days, was separated from another episode by 7 or more days, and was accompanied by either signs of dehydration (sunken eyes, slow recoil after an abdominal "skin pinch" or administration of intravenous fluids), dysentery or admission to hospital based on clinical concern of diarrheal disease severity.

Procedures

Stools or rectal swabs from cases and controls were cultured onto MacConkey and xylose/lysine/deoxycholate agar and three *E. coli* colonies per subject were identified and pooled for extraction of DNA. The DNA then was tested by a multiplex PCR containing primers to amplify eltB (LTB subunit) and est (ST). ETEC strains were shipped to the University of Chile and confirmed by PCR to detect LT and ST variants (STh and STp). Confirmed ETEC isolates were further tested by monoplex or multiplex PCRs using primers that detect target genes encoding the major CFs (CFA/I, CFA/II [CS1, CS2, CS3], CFA/IV [CS4, CS5, CS6]), and various minor CFs (CS7, CS12, CS13, CS14, CS17, CS18, CS19, CS20, CS21 and CS30) (Table 3, below).

Reference strains served as positive controls for specific CFs. Crude bacterial lysate was obtained by boiling 5 pooled colonies of each ETEC isolate in 0.1% TRITON™ X-100 (detergent) for 10 minutes, followed by centrifugation at 8000×g for 5 minutes to separate the template DNA in the supernatant from the cellular debris. PCR was performed with total bacterial DNA in a 25-μL reaction, containing 10 mmol/L deoxyribonucleotide triphosphate (dNTP) mix, 30 mmol/L $MgCl_2$, x reaction buffer (10 mmol/L Tris-HCl, 50 mmol/L KCl), 1 U of Taq polymerase (GoTaq; PROMEGA™, Madison, Wis.), and 1 μL of template DNA. Primers were used at concentrations shown in Table 3, below. To prevent nonspecific amplification, the "hot start" technique was used. This includes preheating the reaction mixture to 94° C. for 5 minutes before adding Taq DNA polymerase. Samples were amplified for 35 cycles, with each cycle comprising 90 seconds at 94° C. for denaturation, 30 seconds at specific primers annealing temperatures, 60 seconds at 68° C. for strand elongation, and a final extension at 72° C. for 5 minutes. PCR products were electrophoresed in 2.0% agarose, stained with ethidium bromide, and amplicons identified based on expected size of the amplified product and compared with amplicons of reference strains.

Isolates were agglutinated with specific anti-O antisera. A subset of isolates were tested at the University of Gothenburg, Sweden to assess phenotypic expression of CFs using monoclonal antibodies.

TABLE 3

Primers used for detection of toxin and colonization factor genes in ETEC strains.

| Gene (Toxin/CFs) | For/Rev | Sequence (5' - 3') | SEQ ID NO | Contion (pmol/μL) | PCR Type (Mn/Mt) | Product Size (bp) | Ref |
|---|---|---|---|---|---|---|---|
| eltB (LT) | F | GCACACGGAGCTCCTCAGT | 1 | 0.2 | Mn | 218 | Vidal et al.[18] |
| | R | TCCTTCATCCTTTCAATGGCTTT | 2 | | | | |
| sta2 (STh) | F | TTCTTTCTGTATTGTCTTTTTCACC | 3 | 0.2 | Mn | 193 | Vidal et al.[18] |
| | R | TAATAGCACCCGGTACAAGCAG | 4 | | | | |
| sta1 (STp) | F | CCTCGACATATAACATGATGCAACTC | 5 | 0.2 | Mn | 127 | This Study |
| | R | AAATTGCCAACATTAGCTTTTTCA | 6 | | | | |
| cfaB (CFA/I) | F | ACTATTGGTGCAATGGCTCTGAC | 7 | 0.2 | Mt1 | 497 | Vidal et al.[18] |
| | R | CAGGATCCCAAAGTCATTACAAG | 8 | | | | |
| cooA (CS1) | F | GAGAAGACCATTAGCGTTACGG | 9 | 0.13 | Mt3 | 410 | Vidal et al.[18] |
| | R | CCCTGATATTGACCAGCTGTTAG | 10 | | | | |
| cotA (CS2) | F | ACTGTAACTGCTAGCGTTGATCC | 11 | 0.2 | Mt1 | 358 | Vidal et al.[18] |
| | R | TGCTTCCTGCATTAATAACGAGT | 12 | | | | |
| cstH (CS3) | F | CCCACTCTAACCAAAGAACTGG | 13 | 0.48 | Mt3 | 300 | Vidal et al.[18] |
| | R | CGTATTTCCAGCATTTTTATCCA | 14 | | | | |
| csaB (CS4) | F | ATTGATATTTTGCAAGCTGATGG | 15 | 0.32 | Mt3 | 242 | Vidal et al.[18] |
| | R | GTCACATCTGCGGTTGATAGAGT | 16 | | | | |
| csfA (CS5) | F | TCCGCTCCCGTTACTCAG | 17 | 0.2 | Mt2 | 226 | Sjoling et al.[20] |
| | R | GAAAAGCGTTCACACTGTTTATATT | 18 | | | | |
| cssA (CS6) | F | AAATGTATCCCAGGTAACGGTCT | 19 | 0.2 | Mt2 | 165 | Vidal et al.[18] |
| | R | TGTTGATTAGGCGTAACCTCTGT | 20 | | | | |
| csvA (CS7) | F | TGCTCCCGTTACTAAAAATAC | 21 | 0.16 | Mt4 | 203 | Del Canto et al.[11] |
| | R | TAGATGTCGTATCACTACGT | 22 | | | | |
| cswA (CS12) | F | GCGAATAACAATGATGCAAG | 23 | 0.16 | Mt4 | 263 | Del Canto et al.[11] |
| | R | CCTGACTGGTTTACAAGATA | 24 | | | | |
| cshE (CS13) | F | GGGACTGCCACAATGAATTT | 25 | 0.4 | Mn | 178 | Sjoling et al.[20] |
| | R | CAGCACCACCTGCTGATTTA | 26 | | | | |
| csuA1 (CS14) | F | TTTGCAACCGACATCTACCA | 27 | 0.4 | Mn | 162 | Sjoling et al.[20] |
| | R | CCGGATGTAGTTGCTCCAAT | 28 | | | | |
| csbA-csdA (CS17-19) (CS17) | F | TAAACTTGATCTTCTGCAAGC | 29 | 0.16 | Mt4 | 348 | Del Canto et al.[11] |
| | R | TCAGGCGCAGTTCCTTGTGT | 30 | | | | |
| csbA-csdA (CS17-19) csbA (CS19) | F | GCATGAATCGTAAGCTGTTG | 31 | 0.16 | Mn | 324 | Del Canto et al.[11] |
| | R | GCATGAATCGTAAGCTGTTG | 32 | | | | |
| fotG (CS18) | F | ATCCGTCAGGTGTTTGTGGT | 33 | 0.4 | Mn | 362 | Rodas et al.[21] |
| | R | CACCTGAATTCCTCGACAGG | 34 | | | | |
| csnA (CS20) | F | AGGTATCCAAATCCGCACTG | 35 | 0.4 | Mn | 114 | Sjöling et al.[20] |
| | R | CATCAGCCAGCACATAGGAA | 36 | | | | |
| lngA (CS21) | F | TCATGAGCCTGCTGGAAGTTATCA | 37 | 0.16 | Mn | 617 | Pichel et al.[22] |
| | R | TCCGGCTACCTAAAGTAATTGAGT | 38 | | | | |
| csmA (CS30) | F | CCACTTTCTTCCAGCAACCA | 39 | 0.2 | Mt | 219 | von Mentzer et al[14] |
| | R | CCTTGGTACCATTGCTGGTT | 40 | | | | |

Cfs: colonization factors; Mn = monoplex PCR; Mt = multiplex PCR.

Data Analysis

Analyses were restricted to ETEC cases that had a single ETEC toxin/CF genotype pattern. Prevalence of ETEC CFs was expressed as percentages in a stratified analysis by ETEC toxin profile, site and region. Strength of association between ETEC toxin and CF genotypes and MSD was examined using conditional logistic regression models in which the outcome was case-control status (MSD) and the independent variable (covariate) was whether the child's ETEC had the specific CFA (no or yes), while applying Firth's penalized likelihood approach. Matched odds ratios (ORs) and corresponding 95% confidence intervals (CIs) were obtained from these models. Pooled and site-specific analyses were conducted. Heterogeneity in ORs across the sites was examined using Chi square test for heterogeneity. A p value ≤0.05 was considered significant. Data were analyzed using SPSS version 23 (IBM™, Inc.) and SAS statistical software version 9.4 (SAS INSTITUTE™ Inc. Cary, N.C., USA).

Example 2. Major CFs Among ETEC from MSD Cases and Controls

Table 4, below, summarizes the proportion of ETEC strains that carry the major CF antigens including CFA/I and CS1-CS6, with data presented by country, continent and toxin genotype. Overall, 363 (66.2%) of 548 ST-only and LT/ST strains encoded a major CF antigen including 20.4% encoding CFA/I, 14.1% encoding CFA/II (i.e., CS3 alone or with CS1 or CS2) and 31.8% encoding CFA/IV (i.e., CS6 alone or with CS4 or CS5). The only major CF commonly observed among LT-only isolates was CS6-only, which was recorded in 44 of 258 LT-only strains (17.1%). Only 3 of 258 LT-only strains (1.2%) encoded CFA/I or CFA/II.

Among a subset of 123 ETEC isolates from MSD cases shown by PCR to encode major CFs, 96 phenotypically expressed the CF surface antigens detected by dot blot immunoassays. These included 24/26 CFA/I (92.3%), 4/7 CSI (57.1%), 10/11 CS2 (90.9%), 13/17 CS3 (76.5%), 19/23 CS5 (82.6%) and 26/39 CS6 (66.7%) isolates; no isolates encoding CS4 were tested.

TABLE 4

Prevalence of major colonization factors, by toxin profiles of ETEC strains from MSD cases from individual GEMS sites.

| Site | Toxin Profile | No. Cases | CFA/I | Any CFA/II[a] | CS3-only | CS1 + CS3 | CS2 + CS3 |
|---|---|---|---|---|---|---|---|
| Gambia | LT-only | 35 | 0/35 (0%) | 1/35 (2.9%) | 0/35 (0%) | 0/35 (0%) | 1/35 (2.9%) |
| | ST-only | 46 | 16/46 (34.8%) | 0/46 (0%) | 0/46 (0%) | 0/46 (0%) | 0/46 (0%) |
| | LT/ST | 39 | 0/39 (0%) | 14/39 (35.9%) | 6/39 (15.4%) | 1/39 (2.6%) | 7/39 (17.9%) |
| | ST + LT/ST | 85 | 16/85 (18.8%) | 14/85 (16.5%) | 6/85 (7.1%) | 1/85 (1.2%) | 7/85 (8.2%) |
| | Total | 120 | 16/120 (13.3%) | 15/120 (12.5%) | 6/120 (5.0%) | 1/120 (0.8%) | 8/120 (6.7%) |
| Mali | LT-only | 51 | 1/51 (2.0%) | 0/51 (0%) | 0/51 (0%) | 0/51 (0%) | 0/51 (0%) |
| | ST-only | 46 | 17/46 (37.0%) | 0/46 (0%) | 0/46 (0%) | 0/46 (0%) | 0/46 (0%) |
| | LT/ST | 41 | 4/41 (9.8%) | 6/41 (14.6%) | 1/41 (2.4%) | 1/41 (2.4%) | 4/41 (9.8%) |
| | ST + LT/ST | 87 | 21/87 (24.1%) | 6/87 (6.9%) | 1/87 (1.1%) | 1/87 (1.1%) | 4/87 (4.6%) |
| | Total | 138 | 22/138 (15.9%) | 6/138 (4.3%) | 1/138 (0.7%) | 1/138 (0.7%) | 4/138 (2.9%) |
| Mozambique | LT-only | 16 | 0/16 (0%) | 0/16 (0%) | 0/16 (0%) | 0/16 (0%) | 0/16 (0%) |
| | ST-only | 22 | 9/22 (40.9%) | 0/22 (0%) | 0/22 (0%) | 0/22 (0%) | 0/22 (0%) |
| | LT/ST | 25 | 0/25 (0%) | 8/25 (32.0%) | 1/25 (4.0%) | 2/25 (8.0%) | 5/25 (20.0%) |
| | ST + LT/ST | 47 | 9/47 (19.1%) | 8/47 (17.0%) | 1/47 (2.1%) | 2/47 (4.3%) | 5/47 (10.6%) |
| | Total | 63 | 9/63 (14.3%) | 8/63 (12.7%) | 1/63 (1.6%) | 2/63 (3.2%) % ) | 5/63 (7.9%) |
| Kenya | LT-only | 69 | 0/69 (0%) | 0/69 (0%) | 0/69 (0%) | 0/69 (0%) | 0/69 (0%) |
| | ST-only | 68 | 24/68 (35.3%) | 0/68 (0%) | 0/68 (0%) | 0/68 (0%) | 0/68 (0%) |
| | LT/ST | 52 | 2/52 (3.8%) | 18/52 (34.6%) | 2/52 (3.8%) | 9/52 (17.3%) | 7/52 (13.5%) |
| | ST + LT/ST | 120 | 26/120 (21.7%) | 18/120 (15.0%) | 2/120 (1.7%) | 9/120 (7.5%) | 7/120 (5.8%) |
| | Total | 189 | 28/189 (14.5%) | 18/189 (9.5%) | 2/189 (1.1%) | 9/189 (4.8%) | 7/189 (3.7%) |
| Africa | LT | 171 | 1/171 (0.6%) | 1/171 (0.6%) | 0/171 (0%) | 0/171 (0%) | 1/171 (0.6%) |
| | ST | 182 | 66/182 (36.3%) | 0/182 (0%) | 0/182 (0%) | 0/182 (0%) | 0/182 (0%) |
| | LT/ST | 157 | 6/157 (3.8%) | 46/157 (29.3%) | 10/157 (6.4%) | 13/157 (8.3%) | 23/157 (14.6%) |
| | ST + LT/ST | 339 | 72/339 (21.2%) | 46/339 (13.6%) | 10/339 (2.9%) | 13/339 (3.8%) | 23/339 (6.8%) |
| | Total | 510 | 73/510 (14.3%) | 47/510 (9.2%) | 10/510 (2.0%) | 13/510 (2.5%) | 24/510 (4.7%) |
| India | LT-only | 26 | 0/26 (0%) | 0/26 (0%) | 0/26 (0%) | 0/26 (0%) | 0/26 (0%) |
| | ST-only | 36 | 13/36 (36.1%) | 0/36 (0%) | 0/36 (0%) | 0/36 (0%) | 0/36 (0%) |
| | LT/ST | 44 | 3/44 (6.8%) | 19/44 (43.2%) | 6/44 (13.6%) | 6/44 (13.6%) | 7/44 (15.9%) |
| | ST + LT/ST | 80 | 16/80 (20.0%) | 19/80 (23.8%) | 6/80 (7.5%) | 6/80 (7.5%) | 7/80 (8.8%) |
| | Total | 106 | 16/106 (15.1%) | 19/106 (17.9%) | 6/106 (5.7%) | 6/106 (5.7%) | 7/106 (6.6%) |
| Bangladesh | LT-only | 18 | 0/18 (0%) | 0/18 (0%) | 0/18 (0%) | 0/18 (0%) | 0/18 (0%) |
| | ST-only | 15 | 5/15 (33.3%) | 1/15 (6.7%) | 0/15 (0%) | 0/15 (0%) | 1/15 (6.7%) |
| | LT/ST | 23 | 1/23 (4.3%) | 5/23 (21.7%) | 0/23 (0%) | 3/23 (13.0%) | 2/23 (8.7%) |
| | ST + LT/ST | 38 | 6/38 (15.8%) | 6/38 (15.8%) | 0/38 (0%) | 3/38 (7.9%) | 3/38 (7.9%) |
| | Total | 56 | 6/56 (10.7%) | 6/56 (10.7%) | 0/56 (0%) | 3/56 (5.4%) | 3/56 (5.4%) |
| Pakistan | LT-only | 43 | 0/43 (0%) | 1/43 (2.3%) | 0/43 (0%) | 1/43 (2.3%) | 0/43 (0%) |

TABLE 4-continued

Prevalence of major colonization factors, by toxin profiles of ETEC strains from MSD cases from individual GEMS sites.

|  |  |  |  |  |  |  |  |
|---|---|---|---|---|---|---|---|
|  | ST-only | 58 | 17/58 (29.3%) | 0/58 (0%) | 0/58 (0%) | 0/58 (0%) | 0/58 (0%) |
|  | LT/ST | 33 | 1/33 (3.0%) | 6/33 (18.2%) | 1/33 (3.0%) | 0/33 (0%) | 5/33 (15.2%) |
|  | ST+ | 91 | 18/91 (19.8%) | 6/91 (6.6%) | 1/91 (1.1%) | 0/91 (0%) | 5/91 (5.5%) |
|  | LT/ST | 134 | 18/134 (13.4%) | 7/134 (5.2%) | 1/134 (0.7%) | 1/134 (0.7%) | 5/134 (3.7%) |
|  | Total |  |  |  |  |  |  |
| Asia | LT-only | 87 | 0/87 (0%) | 1/87 (1.1%) | 0/87 (0%) | 1/87 (1.1%) | 0/87 (0%) |
|  | ST-only | 109 | 35/109 (32.1%) | 1/109 (0.9%) | 0/109 (0.9%) | 0/109 (0%) | 1/109 (0.9%) |
|  | LT/ST | 100 | 5/100 (5.0%) | 30/100 (30.0%) | 7/100 (7.0%) | 9/100 (9.0%) | 14/100 (14.0%) |
|  | ST + LT/ST | 209 | 40/209 (19.1%) | 31/209 (14.8%) | 7/209 (3.3%) | 9/209 (4.3%) | 15/209 (7.2%) |
|  | Total | 296 | 40/296 (13.5%) | 32/296 (10.8%) | 7/296 (2.4%) | 10/296 (3.4%) | 15/296 (5.1%) |
| Africa/Asia | LT-only | 258 | 1/258 (0.4%) | 2/258 (0.8%) | 0/258 (0%) | 1/258 (0.4%) | 1/258 (0.4%) |
|  | ST-only | 291 | 101/291 (34.7%) | 1/291 (0.3%) | 0/291 (0%) | 0/291 (0%) | 1/291 (0.3%) |
|  | LT/ST | 257 | 11/257 (4.3%) | 76/257 (29.6%) | 17/257 (6.6%) | 22/257 (8.6%) | 37/257 (14.4%) |
|  | ST + LT/ST | 548 | 112/548 (20.4%) | 77/548 (14.1%) | 17/548 (3.1%) | 22/548 (4.0%) | 38/548 (6.9%) |
|  | Total | 806 | 113/806 (14.0%) | 79/806 (9.8%) | 17/806 (2.1%) | 23/806 (2.9%) | 39/806 (4.8%) |

| Site | Toxin Profile | No. Cases | Any CFA/IV[b] | CS6-only | CS4 + CS6 | CS5 + CS6 |
|---|---|---|---|---|---|---|
| Gambia | LT-only | 35 | 7/35 (20.0%) | 5/35 (14.3%) | 0/35 (0%) | 2/35 (5.7%) |
|  | ST-only | 46 | 17/46 (37.0%) | 3/46 (6.5%) | 0/46 (0%) | 14/46 (30.4%) |
|  | LT/ST | 39 | 14/39 35.9%) | 5/39 (12.8%) | 0/39 (0%) | 9/39 (23.1%) |
|  | ST + LT/ST | 85 | 32/85 (37.2%) | 8/85 (9.4%) | 0/85 (0%) | 23/85 (27.1%) |
|  | Total | 120 | 38/120 (31.7%) | 13/120 (10.8%) | 0/120 (0%) | 25/120 (20.8%) |
| Mali | LT-only | 51 | 15/51 (29.4%) | 14/51 (27.5%) | 0/51 (0%) | 1/51 (2.0%) |
|  | ST-only | 46 | 20/46 (43.5%) | 6/46 (13.0%) | 0/46 (0%) | 14/46 (30.4%) |
|  | LT/ST | 41 | 12/41 (29.3%) | 2/41 (4.9%) | 3/41 (7.3%) | 7/41 (17.1%) |
|  | ST + LT/ST | 87 | 32/87 (36.8%) | 8/87 (9.2%) | 3/87 (3.4%) | 21/87 (24.1%) |
|  | Total | 138 | 47/138 (34.1%) | 22/138 (15.9%) | 3/138 (2.2%) | 22/138 (15.9%) |
| Mozambique | LT-only | 16 | 4/16 (25.0%) | 1/16 (6.3%) | 0/16 (0%) | 3/16 (18.8%) |
|  | ST-only | 22 | 4/22 (18.2%) | 3/22 (13.6%) | 0/22 (0%) | 1/22 (4.5%) |
|  | LT/ST | 25 | 13/25 (52.0%) | 2/25 (8.0%) | 0/25 (0%) | 11/25 (44.0%) |
|  | ST + LT/ST | 47 | 17/47 (36.2%) | 5/47 (10.6%) | 0/47 (0%) | 12/47 (25.5%) |
|  | Total | 63 | 21/63 (33.3%) | 6/63 (9.5%) | 0/63 (0%) | 15/63 (23.8%) |
| Kenya | LT-only | 69 | 16/69 (23.2%) | 11/69 (15.9%) | 0/69 (0%) | 5/69 (7.2%) |
|  | ST-only | 68 | 13/68 (19.1%) | 4/68 (5.9%) | 0/68 (0%) | 9/68 (13.2%) |
|  | LT/ST | 52 | 14/52 (26.9%) | 4/52 (7.7%) | 1/52 (1.9%) | 9/52 (17.3%) |
|  | ST + LT/ST | 120 | 27/120 (22.5%) | 8/120 (6.7%) | 1/120 (0.8%) | 18/120 (15.0%) |
|  | Total | 189 | 43/189 (22.8%) | 19/189 (10.1%) | 1/189 (0.5%) | 23/189 (12.2%) |
| Africa | LT | 171 | 42/171 (24.6%) | 31/171 (18.1%) | 0/171 (0%) | 11/171 (6.4%) |
|  | ST | 182 | 54/182 (29.7%) | 16/182 (8.8%) | 0/182 (0%) | 38/182 (20.9%) |
|  | LT/ST | 157 | 53/157 (33.8%) | 13/157 (8.3%) | 4/157 (2.5%) | 36/157 (22.9%) |
|  | ST + LT/ST | 339 | 107/339 (31.6%) | 29/339 (86%) | 4/339 (1.2%) | 74/339 (21.8%) |
|  | Total | 510 | 149/510 (29.2%) | 60/510 (11.8%) | 4/510 (0.8%) | 85/510 (16.7%) |
| India | LT-only | 26 | 8/26 (30.8%) | 5/26 (19.2%) | 0/26 (0%) | 3/26 (11.5%) |
|  | ST-only | 36 | 8/36 (22.2%) | 5/36 (13.9%) | 1/36 (2.8%) | 2/36 (5.6%) |
|  | LT/ST | 44 | 13/44 (29.5%) | 6/44 (13.6%) | 0/44 (0%) | 7/44 (15.9%) |
|  | ST + LT/ST | 80 | 21/80 (26.3%) | 11/80 (13.8%) | 1/80 (1.3%) | 9/80 (11.3%) |
|  | Total | 106 | 29/106 (27.4%) | 16/106 (15.1%) | 1/106 (0.9%) | 12/106 (11.3%) |
| Bangladesh | LT-only | 18 | 2/18 (11.1%) | 1/18 (5.6%) | 0/18 (0%) | 1/18 (5.6%) |
|  | ST-only | 15 | 5/15 (33.3%) | 4/15 (26.7%) | 0/15 (0%) | 1/15 (6.7%) |
|  | LT/ST | 23 | 7/23 (30.4%) | 1/23 (4.3%) | 0/23 (0%) | 6/23 (26.1%) |
|  | ST + LT/ST | 38 | 12/38 (31.6%) | 5/38 (13.2%) | 0/38 (0%) | 7/38 (18.4%) |
|  | Total | 56 | 14/56 (25.0%) | 6/56 (10.7%) | 0/56 (0%) | 8/56 (14.3%) |
| Pakistan | LT-only | 43 | 9/43 (20.9%) | 7/43 (16.3%) | 0/43 (0%) | 2/43 (4.7%) |
|  | ST-only | 58 | 18/58 (31.0%) | 8/58 (13.8%) | 2/58 (3.4%) | 8/58 (13.8%) |
|  | LT/ST | 33 | 16/33 (48.5%) | 2/33 (6.1%) | 1/33 (3.0%) | 13/33 (39.4%) |
|  | ST+ | 91 | 34/91 (37.4%) | 10/91 (11.0%) | 3/91 (3.3%) | 21/91 (23.1%) |
|  | LT/ST | 134 | 43/134 (32.1%) | 17/134 (12.7%) | 3/134 (2.2%) | 23/134 (17.2%) |
|  | Total |  |  |  |  |  |
| Asia | LT-only | 87 | 19/87 (21.8%) | 13/87 (14.9%) | 0/87 (0%) | 6/87 (6.9%) |
|  | ST-only | 109 | 31/109 (28.4%) | 17/109 (15.6%) | 3/109 (2.8%) | 11/109 (10.0%) |
|  | LT/ST | 100 | 36/100 36.0%) | 8/100 (8.0%) | 1/100 (1.0%) | 26/100 (26.0%) |
|  | ST + LT/ST | 209 | 67/209 (32.1%) | 25/209 (12.0%) | 4/209 (1.9%) | 37/209 (17.7%) |
|  | Total | 296 | 86/296 (29.1%) | 38/296 (12.8%) | 4/296 (1.4%) | 43/296 (14.5%) |
| Africa/Asia | LT-only | 258 | 61/258 (23.6%) | 44/258 (17.1%) | 0/258 (0%) | 17/258 (6.6%) |
|  | ST-only | 291 | 85/291 (29.2%) | 33/291 (11.3%) | 3/291 (1.0%) | 49/291 (16.8%) |

TABLE 4-continued

Prevalence of major colonization factors, by toxin profiles of ETEC strains
from MSD cases from individual GEMS sites.

| | | | | | |
|---|---|---|---|---|---|
| LT/ST | 257 | 89/257 (34.6%) | 22/257 (8.6%) | 5/257 (1.9%) | 62/257 (24.1%) |
| ST + LT/ST | 548 | 174/548 (31.8%) | 55/548 (10.0%) | 8/548 (1.5%) | 111/548 (20.3%) |
| Total | 806 | 235/806 (29.2%) | 99/806 (12.3%) | 8/806 (1.0%) | 128/806 (15.9%) |

[a]CFA/II strains are defined as encoding CS3 either alone or in combination with either CS1 or CS2 but never both CS1 and CS2. Very rarely isolates that encode CS1 without CS3 have been reported.[19] The rare CFs of this nature recovered in GEMS are not included in this table.
[b]CFA/IV strains are defined as encoding CS6 either alone or in combination with either CS4 or CS5, but never both CS4 and CS5. Very rarely isolates that encode CS5 without CS6 have been reported. The few such isolates recovered in GEMS are not included in this table Example 3. Minor CFs Among ETEC Case Isolates Lacking Major CFs Recognizing that 33.8% of ST-only and LT/ST strains and about 75.2% of LT-only strains do not encode a major CF, the proportion of those isolates that encoded solely one of the following characterized minor CF antigens: CS7, CS12, CS13, CS14, CS17, CS18, CS19, CS20, CS21 or CS30 was investigated. The proportion of ETEC MSD cases that had isolates encoding one of these minor CFs in the absence of a major CF and that accounted for ≥5.0% of the overall case isolates of that toxin genotype (Table 5) was determined. Among MSD cases with ST-only ETEC, only CS14, identified in 58 ST-only cases (19.9%), reached a prevalence of ≥5% (Table 5); seven of 81 cases with LT/ST isolates lacking major CFs (2.7%) also encoded CS14 alone. When encoded as the sole CS, the other minor CS antigens were uncommon (<5%) among ST-only and LT/ST isolates. See Table 5, below.

TABLE 5

Major and minor colonization factors among ETEC isolates of different toxin genotypes, all sites combined.

| | Case isolates (N = 806) | Isolates with major CFs (CFA/I, CS1-CS6) | Isolates without major CFs | CS7-only[a] | CS12-only[a] | CS13-only[a] | CS14-only[a] | CS17-only[a] | CS18-only[a] | CS19-only[a] | CS20-only[a] | CS21-only[a] | CS30-Only | Isolates without major or minor CFs |
|---|---|---|---|---|---|---|---|---|---|---|---|---|---|---|
| LT-only | 258 | 64 (24.8%)[b] | 194 (75.2%)[b] | 20 (7.8%)[b] | 5 (1.9%)[b] | 4 (1.6%)[c] | 11 (4.3%)[b] | 17 (6.6%)[b] | 4 (1.6%)[c] | 0 (0%)[c1] | 24 (9.5%)[c] | 4 (1.6%)[b] | — | 105 (40.7%)[b] |
| ST-only | 291 | 187 (64.3%)[d] | 104 (35.7%)[d] | 0 (0%)[d] | 0 (0%)[d] | 0 (0%)[e] | 58 (19.9%)[d] | 1 (0.3%)[e] | 1 (0.3%)[e] | 0 (0%)[e1] | 2 (0.7%)[e] | 5 (1.7%)[d] | — | 37 (12.7%)[d] |
| LT/ST | 257 | 176 (68.5%)[f] | 81 (31.5%)[f] | 1 (0.4%)[f] | 9 (3.5%)[f] | 2 (0.8%)[g] | 7 (2.7%)[f] | 0 (0%)[f] | 5 (2.0%)[g] | 1 (0.4%)[g1] | 9 (3.5%)[g] | 2 (0.8%)[f] | 3 (1.2%)[g] | 42 (16.3%)[f] |
| ST-only + LT/ST | 548 | 363 (66.2%)[h] | 185 (33.8%)[h] | 1 (0.2%)[h] | 9 (1.6%)[h] | 2 (0.4%)[i] | 65 (11.9%)[h] | 1 (0.2%)[h] | 6 (1.1%)[i] | 1 (0.2%)[i1] | 11 (2.0%)[i] | 7 (1.3%)[h] | — | 79 (14.4%)[h] |

[a1]Percent of 502 ST-only plus LT/ST strains;

[b]Percent of all 258 LT-only strains

[c]Percent of 252 LT-only strains (6 strains were not recoverable from −70° C. storage for testing);

[c1]Percent of 225 LT-only strains;

[d]Percent of all 291 ST-only strains;

[e]Percent of 290 ST-only strains (1 strain was not recoverable from −70° C. storage for testing);

[e1]Percent of 266 ST-only strains;

[f]Percent of all 257 LT/ST strains;

[g]Percent of 255 LT/ST strains (2 strains were not recoverable from −70° C. storage for testing);

[g1]Percent of 236 LT/ST strains;

[h]Percent of all 548 ST-only plus LT/ST strains;

[i]Percent of 545 ST-only plus LT/ST strains (3 strains were not recoverable from −70° C. storage for testing).

Example 4. Conditional Logistic Regression Analyses to Assess the Strength of Association Between CF-Toxin Genotypes and MSD Among ST-only and LT/ST ETEC strains encoding a single minor CF but no major CFs, only CS14 was significantly associated with MSD (Table 6).

TABLE 6

Odds ratios for association with moderate-to-severe diarrhea of ETEC encoding major and minor colonization factors in combination with different toxin genotypes.

| Major Colonization Factors | Toxin Type | Cases (n = 9439) | Controls (n = 13,129) | Pooled Matched Odds Ratio (95% C1) | p value | p value for heterogeneity[a] |
|---|---|---|---|---|---|---|
| CFA/I | ST-only + LT/ST | 112 (1.19%) | 26 (0.20%) | 1.85 (1.52-2.22) | <0.0001 | 0.98 |
| Any CFA/II | ST-only + LT/ST | 77 (0.82%) | 55 (0.43%) | 1.36 (1.08-1.69) | 0.006 | 0.9 |
| CS3-only | ST-only + LT/ST | 17 (0.18%) | 13 (0.099%) | 1.37 (0.82-2.12)[b1] | 0.18 | 0.87 |
| CS1 + CS3 | ST-only + LT/ST | 22 (0.23%) | 13 (0.99%) | 1.57 (1.01-2.32) | 0.031 | 0.86 |
| CS2 + CS3 | ST-only + LT/ST | 38 (0.40%) | 32 (0.24%) | 1.29 (0.92-1.74) | 0.11 | 0.75 |
| Any CFA/IV | ST-only + LT/ST | 174 (1.84%) | 83 (0.63%) | 1.64 (1.41-1.91) | <0.0001 | 0.84 |
| CS6-only | ST-only + LT/ST | 55 (0.58%) | 39 (0.30%) | 1.48 (1.12-1.91) | <0.004 | 0.86 |
| CS4 + CS6 | ST-only + LT/ST | 8 (0.09%) | 4 (0.03%) | 1.62 (0.76-2.99)[b2] | 0.15 | 0.97 |
| CS5 + CS6 | ST-only + LT/ST | 111 (1.18%) | 41 (0.31%) | 1.74 (1.43-2.09) | <0.0001 | 0.96 |
| CS6-only | LT-only | 44 (0.47%) | 65 (0.50%) | 0.96 (0.71-1.27) | 0.82 | 0.79 |
| CS5 + CS6 | LT-only | 17 (0.18%) | 30 (0.22%) | 0.95 (0.57-1.47) | 0.8 | 0.96 |
| CS7 | ST-only + LT/ST | 1 (0.01%) | 1 (0.01%) | 1.88 (0.21-6.74)[b3] | 0.44 | 0.64 |
| | LT-only | 20 (0.21%) | 12 (0.09%) | 1.49 (0.93-2.23) | 0.072 | 0.93 |
| CS12 | ST-only + LT/ST | 9 (0.10%) | 27 (0.21%) | 0.59 (0.28-1.05)[b4] | 0.10 | 0.86 |
| | LT-only | 5 (0.052%) | 7 (0.05%) | 1.20 (0.45-2.51)[b4] | 0.66 | 0.72 |
| CS13 | ST-only + LT/ST | 2 (0.02%) | 4 (0.03%) | 1.14 (0.23-3.22)[b5] | 0.82 | 0.93 |
| | LT-only | 4 (0.04%) | 29 (0.22%) | 0.35 (0.11-0.77) | 0.026 | 0.41 |
| CS14 | ST-only + LT/ST | 65 (0.69%) | 36 (0.27%) | 1.49 (1.15-1.89) | 0.0014 | 0.69 |
| | LT-only | 11 (0.12%) | 11 (0.08%) | 1.14 (0.60-1.94)[b6] | 0.64 | 0.52 |
| CS17 | ST-only + LT/ST | 1 (0.01%) | 1 (0.01%) | 1.49 (0.17-5.40)[b7] | 0.62 | 0.55 |
| | LT-only | 17 (0.18%) | 16 (0.12%) | 1.21 (0.72-1.87) | 0.42 | 0.73 |
| CS18 | ST-only + | 6 (0.06%) | 7 (0.05%) | 1.19 (0.49-2.36)[b8] | 0.65 | 0.77 |
| | LT-only | 4 (0.04%) | 2 (0.02%) | 1.63 (0.54-3.63)[b8] | 0.29 | 0.71 |
| CS19 | ST-only + LT/ST | 1 (0.01%) | 5 (0.04%) | 0.5 (0.67-2.08)[b9] | 0.51 | 0.49 |
| | LT-only | 0 (0%) | 6 (0.05%) | 0.18 (0.001-1.25)[b9] | 0.23 | 0.53 |
| CS20 | ST-only + LT/ST | 11 (0.12%) | 36 (0.27%) | 0.60 (0.31-1.02) | 0.088 | 0.78 |
| | LT-only | 24 (0.25%) | 29 (0.22%) | 1.12 (0.73-1.64) | 0.55 | 0.87 |
| CS21 | ST-only + LT/ST | 7 (0.07%) | 12 (0.09%) | 0.93 (0.41-1.78) | 0.86 | 0.99 |
| | LT-only | 4 (0.04%) | 0 (0%) | 2.84 (0.95-6.42)[b10] | 0.028 | 0.72 |
| CS30 | LT/ST | 3 (0.03%) | 3 (0.02%) | 1.46 (0.40-3.58) | 0.48 | |

[a]There was no significant heterogeneity across GEMS sites (by chi square test for heterogeneity);

[b1]ST-CS3 only was not detected in Bangladesh.

[b2]ST-CS4 & SC6 was not found Gambia, Mozambique and Bangladesh;

[b3]ST-CS7 only was restricted to Gambia and India;

[b4]ST-CS12 only was not found in Mozambique and LT only-CS12 was not found in Gambia;

[b5]ST-CS13 only was not found in Mali and Pakistan;

[b6]LT only-CS14 only was not found in Mali and Bangladesh;

[b7]ST-CS17 only was found only in Mozambique and Bangladesh;

[b8]ST-SC18 only was not found in Pakistan and LT only-CS18 only was found only in Mali, Kenya and Pakistan;

[b9]ST-CS19 only was detected in Mali, India and Bangladesh, and LT-only-CS19 was found only in Gambia and India;

[b10]LT-only CS21 only was detected only in Kenya and Pakistan;

[c]Excludes strains that co-encoded a major colonization factor such as CFA/I, CFA/II, CFA/IV, and all other minor colonization factors.

Example 5. Deletion Mutants of *S. flexneri* 1b

Genomic DNA isolated from wild type (WT) *S. flexneri* 1b strain 103849 or 204584 was used as a template with primers Wu048 (GTGAAGGTGAAGCCCGTGAAGT; SEQ ID NO:41) and Wu049 (TGCAGCAGCATTGCGGT-TACG; SEQ ID NO:42) to amplify the intact guaBA locus as a 1.8 kb band. Amplification with genomic DNA from the ΔguaBA mutant derivatives (2, 7, 9, 14, 2, 8, 11, 12, and 13) result in an 891 bp band reflecting the 900 bp deletion. NTC: no template controls. See FIG. 1 for results. This amplification of the guaBA locus by PCR confirms the deletion in two isolates of *S. flexneri* 1b.

Figure 2:
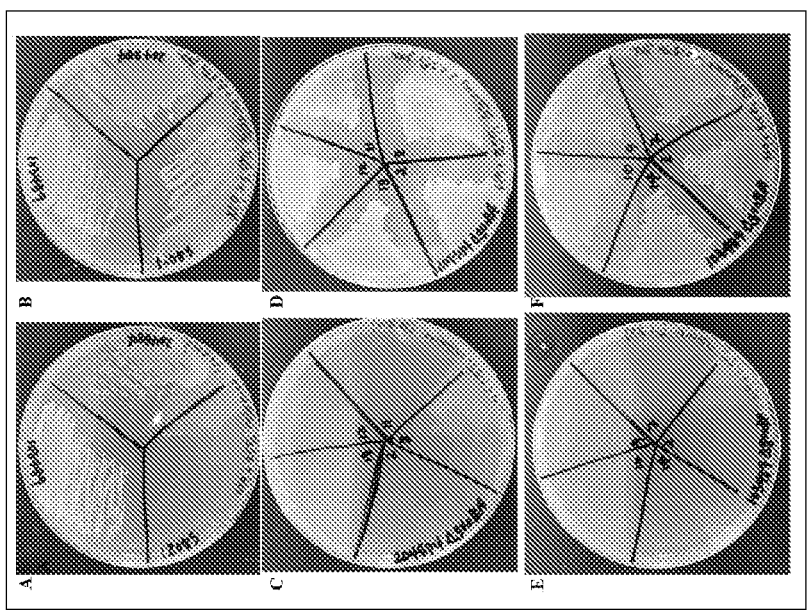
FIG. 2 is a photograph of plates confirming the guanine auxotrophy in *S. flexneri* 1b ΔguaBA vaccine strains.
Figure 3:
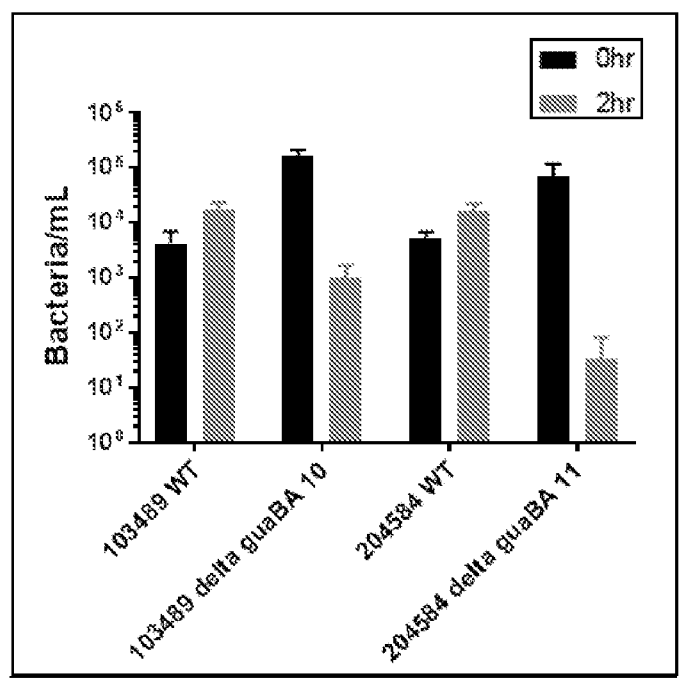
FIG. 3 is a bar graph showing the intracellular replication defect in *S. flexneri* 1b ΔguaBA vaccine strains.

To confirm guanine auxotrophy in the *S. flexneri* 1b ΔguaBA strains, wild type or mutant derivative strains were grown on minimal M9 media plus 0.5% casamino acids with (panels B, D, and F of FIG. 2) or without (panels A, C, and E of FIG. 2) 0.0005% guanine. The results in FIG. 2 show that wild type *S. flexneri* 1b strains 103849 and 204584 grow on media with or without added guanine (see FIG. 2A and FIG. 2B). *S. flexneri* 1b 204585 ΔguaBA mutant derivatives (2, 8, 11, 12, and 13) do not grow on media without added guanine (see FIG. 2C and FIG. 2D), and *S. flexneri* 1b 204585 ΔguaBA mutant derivatives (2, 7, 9, 10, and 14) do not grow on media without added guanine (see FIG. 2E and FIG. 2F). Therefore, *S. flexneri* 2a vaccine strain CVD 1208S (which harbors the same guaBA deletion) can serve as a control strain and does not grow on media without added guanine (FIG. 2A).

To confirm intracellular replication defect in *S. flexneri* 1b ΔguaBA vaccine strains, wild type or mutant derivative strains were applied to monolayers of HT-29 cells for 90 minutes, washed with gentamicin, and incubated for an additional 30 minutes (0 hour) or 2 hours. Cells were lysed and intracellular bacteria quantitated. Mean CFU/mL from triplicate wells is shown for each strain in FIG. 3. The hallmark of wild type *Shigella* infection is the ability to replicate within host cells. These data demonstrate the guaBA vaccine strain cannot replicate in host cells and therefore is attenuated for virulence.

Example 6. Vaccine *Shigella* Strains

The lambda red system described in Datsenko and Wanner, Proc. Natl. Acad. Sci. 97(12):6640-6645, 2000 was used to introduce 3 deletion mutations into two different *S. flexneri* 1b strains (this can be done in any *S. flexneri* 1b strain). Using this deletion system, fragments of DNA flanking the region to be deleted were amplified by PCR and fused to an antibiotic resistance encoding gene which is flanked by FRT sequences. (The accessory plasmids were obtained from Datsenko and Wanner). This fragment is electroporated into *S. flexneri* 1b which contains a helper plasmid that catalyzes recombination between the flanking regions on the fragment with genomic copies. The result is *S. flexneri* with FRT-antibiotic resistance gene-FRT in the genome in place of the sequences targeted for deletion (e.g., guaBA, or sen or set). The antibiotic resistance marker then is deleted by introducing a second helper plasmid that catalyzes recombination between FRT sites. The result is *S. flexneri* 1b with a deletion in guaBA, sen and set (performed in 3 separate steps) with no antibiotic resistance markers.

Example 7. Methods of Vaccine Production

Live attenuated *Shigella* vaccines (*S. flexneri* serotypes 1b) was engineered to contain a deletion in the guaBA operon. The deletion of the enterotoxin encoding gene sen or set can be added to *Shigella* strains. Live attenuated *S. flexneri* 7a vaccine strain also can be engineered with deletions in guaBA and sen. Deletions can be introduced into wild type strains using allelic exchange or using lambda red recombination.

The operon encoding ETEC colonization factor CS14 was amplified using PCR from a wild type ETEC strain and cloned into a commercial cloning plasmid (pBAD). A modification of the Tn7 system is described by McKenzie and Craig (McKenzie 2006). The operon was subsequently cloned from pBAD using restriction digestion, into the plasmid pGRG25-P$_{mLpp}$. Plasmid pGRG25-P$_{mLpp}$ is a modification of the pGRG25 plasmid into which the mLpp promoter has been inserted. The mLpp promoter drives high level constitutive expression of cloned downstream genes.

Introduction of pGRG25-P$_{mLpp}$-CS14 into *S. flexneri* live attenuated strain CVD 1208S was performed to facilitate transposition of the CS14-encdong operon into the *Shigella* chromosome at the attTn7 site downstream from glmS. CVD 1208S::CS14 was confirmed using PCR to amplify the chromosomal region and by sequencing the chromosomal insertion. CS14 also can be inserted into the chromosome of any of the live attenuated *Shigella* vaccine strains by the same methods.

In a second strategy for inducing antibodies to block binding of ETEC expressing CS14, the gene encoding the structural subunit, csuA, was cloned in tandem with the gene encoding the tip adhesin, csuD, downstream. The csuA and csuD genes are not fused; each contains an independent promoter and they are transcribed and translated as individual proteins. The goal was to stabilize tip adhesin expression with the presence of the structural subunit. The two genes were cloned into the expression plasmid pBAD in which gene expression is induced with the addition of arabinose. The plasmid pBAD-CsuA2D, was introduced into *Shigella* vaccine strain CVD 1208S by electroporation.

Example 8. Methods of Vaccine Use

Currently there are no licensed vaccines against *Shigella* or ETEC. Other single pathogen vaccine candidates are in various levels of clinical trials but none supply the broad coverage that will be provided by this vaccine. Five putative major vaccine markets are contemplated for vaccines according to the invention:

a. An enteric traveler's vaccine: The vaccines according to the invention are administered orally to a subject traveling to an area where exposure to organisms causing diarrheal disease is likely. To use the vaccine, two doses can be given, about 10 days apart prior to travel. 1 b. A vaccine to prevent disease in specific populations at risk for *Shigella*: Individuals in custodial institutions, prisons, boarding schools, cruise ships, day camps, or day care centers and the like with suboptimal hygiene are at risk for *Shigella* which may be easily transmitted from person to person due to its extremely low infectious dose (<100 CFU may cause infection). Additional populations that participate in specific sexual practices (e.g. men who have sex with men (MSM)) are at risk from widely circulating MDR strains of *Shigella*. To use the vaccine, one dose (about $10^8$ CFU to about $5 \times 10^{10}$ CFU, advantageously about $10^7$ CFU to about $10^{11}$ CFU, preferably about $10^8$ CFU to about $5 \times 10^{10}$ CFU, or about $5 \times 10^8$ CFU to about $10^{10}$ CFU or about $10^8$ CFU to about $10^9$ CFU, or any dose suitable as determined by the practitioner, depending on the size, exposure, general health, age, or other factors) is administered prior to exposure or prior to admittance to the institution, for example.

c. A vaccine to prevent enteric diseases in the developing world: To reduce disease burden and mortality among children in the developing world, the broad spectrum *Shigella*/ETEC combination vaccine of the invention would be expected to be a cost-effective and practical intervention measure and thus would likely be considered for adoption by the GAVI Alliance. For this use, one dose (about $10^8$ CFU to about $5 \times 10^{10}$ CFU, advantageously about $10^7$ CFU to about $10^{11}$ CFU, preferably about $10^8$ CFU to about $5 \times 10^{10}$ CFU, or about $5 \times 10^8$ CFU to about $10^{10}$ CFU or about $10^8$ CFU to about $10^9$ CFU, or any dose suitable as determined by the practitioner, depending on the size, exposure, general health, age, or other factors) is administered to all children under 5. In infants, it is recommended that a regimen of three doses be administered, one each at 10 weeks, at 14 weeks, and at 9 months of age.

d. A vaccine for use in the case of a natural outbreak: As exemplified by a recent outbreak with a Shiga toxin-expressing *S. sonnei* strain, these enteropathogens can acquire new virulence factors that increase their pathogenic potential. A broad spectrum vaccine has the potential to provide protection against a newly emerged strain that may express a new combination of virulence factors.

e. Category B biodefense vaccine: The U.S. government would be interested in accessing a safe and effective prophylactic tool for use in a broad age range of individuals in the case of an intentional attack with these pathogens. For use in biodefense, or in a spontaneous outbreak of diarrheal disease, one dose (about $10^8$ CFU to about $5 \times 10^{10}$ CFU, advantageously about $10^7$ CFU to about $10^{11}$ CFU, preferably about $10^8$ CFU to about $5 \times 10^{10}$ CFU, or about $5 \times 10^8$ CFU to about $10^{10}$ CFU or about $10^8$ CFU to about $10^9$ CFU, or any dose suitable as determined by the practitioner, depending on the size, exposure, general health, age, or other factors) is administered prior to exposure.

REFERENCES

All references listed below and throughout the specification are hereby incorporated by reference in their entirety.

1. Kotloff K L, Nataro J P, Blackwelder W C, Nasrin D, Farag T H, Panchalingam S, et al. Burden and aetiology of diarrhoeal disease in infants and young children in developing countries (the Global Enteric Multicenter Study, GEMS): a prospective, case-control study. Lancet. 2013; 382(9888):209-22.
2. Hyams K C, Bourgeois A L, Merrell B R, Rozmahel R, Escamilla J, Thornton S A, et al. Diarrheal disease during Operation Desert Shield. N Engl J Med. 1991; 325:1423-8.
3. Levine M M. *Escherichia coli* that cause diarrhea: enterotoxigenic, enteropathogenic, enteroinvasive, enterohemorrhagic, and enteroadherent. J Infect Dis. 1987; 155:377-89.
4. Levine M M, Ristaino P, Marley G, Smyth C, Knutton S, Boedeker E, et al. Coli surface antigens 1 and 3 of colonization factor antigen II-positive enterotoxigenic *Escherichia coli*: morphology, purification, and immune responses in humans. Infect Immun. 1984; 44:409-20.
5. Sincock S A, Hall E R, Woods C M, O'Dowd A, Poole S T, McVeigh A L, et al. Immunogenicity of a prototype enterotoxigenic *Escherichia coli* adhesin vaccine in mice and nonhuman primates. Vaccine. 2016; 34(2):284-91.
6. Lundgren A, Bourgeois L, Carlin N, Clements J, Gustafsson B, Hartford M, et al. Safety and immunogenicity of an improved oral inactivated multivalent enterotoxigenic *Escherichia coli* (ETEC) vaccine administered alone and together with dmLT adjuvant in a double-blind, randomized, placebo-controlled Phase I study. Vaccine. 2014; 32(52):7077-84.
7. Turner A K, Stephens J C, Beavis J C, Greenwood J, Gewert C, Randall R, et al. Generation and characterization of a live attenuated enterotoxigenic *Escherichia coli* combination vaccine expressing six colonization factors and heat-labile toxin subunit B. Clin Vaccine Immunol. 2011; 18(12):2128-35.
8. Barry E M, Altboum Z, Losonsky G, Levine M M. Immune responses elicited against multiple enterotoxigenic *Escherichia coli* fimbriae and mutant LT expressed in attenuated *Shigella* vaccine strains. Vaccine. 2003; 21(5-6):333-40.
9. Duan Q, Lu T, Garcia C, Yanez C, Nandre R M, Sack D A, et al. Co-administered Tag-Less Toxoid Fusion 3×STaN12S-mnLTR192G/L211A and CFA/III/IV MEFA (Multiepitope Fusion Antigen) Induce Neutralizing Antibodies to 7 Adhesins (CFA/I, CS1-CS6) and Both Enterotoxins (LT, STa) of Enterotoxigenic *Escherichia coli* (ETEC). Front Microbiol. 2018; 9:1198. doi: 10.3389/fmicb.2018.01198. eCollection;%2018.:1198.
10. Taxt A M, Diaz Y, Aasland R, Clements J D, Nataro J P, Sommerfelt H, et al. Towards Rational Design of a Toxoid Vaccine against the Heat-Stable Toxin of *Escherichia coli*. Infect Immun. 2016; 84(4):1239-49.
11. Robbins J B, Schneerson R, Szu S C. Perspective: hypothesis: serum IgG antibody is sufficient to confer protection against infectious diseases by inactivating the inoculum. J Infect Dis. 1995; 171(6):1387-98.
12. McKenzie R, Porter C K, Cantrell J A, Denearing B, O'Dowd A, Grahek S L, et al. Volunteer challenge with enterotoxigenic *Escherichia coli* that express intestinal colonization factor fimbriae CS17 and CS19. J Infect Dis. 2011; 204(1):60-4.
13. Steinsland H, Valentiner-Branth P, Perch M, Dias F, Fischer T K, Aaby P, et al. Enterotoxigenic *Escherichia coli* infections and diarrhea in a cohort of young children in Guinea-Bissau. J Infect Dis. 2002; 186(12):1740-7.
14. Mansour A, Shaheen H I, Amine M, Hassan K, Sanders J W, Riddle M S, et al. Pathogenicity and phenotypic characterization of enterotoxigenic *Escherichia coli* isolates from a birth cohort of children in rural Egypt. J Clin Microbiol. 2014; 52(2):587-91.
15. Gaastra W, Svennerholm A M. Colonization factors of human enterotoxigenic *Escherichia coli* (ETEC). Trends Microbiol. 1996; 4(11):444-52.
16. del Canto F., Valenzuela P, Cantero L, Bronstein J, Blanco J E, Blanco J, et al. Distribution of classical and nonclassical virulence genes in enterotoxigenic *Escherichia coli* isolates from Chilean children and tRNA gene screening for putative insertion sites for genomic islands. J Clin Microbiol. 2011; 49(9):3198-203.
17. del Canto F., O'Ryan M, Pardo M, Torres A, Gutierrez D, Cadiz L, et al. Chaperone-Usher Pili Loci of Colonization Factor-Negative Human Enterotoxigenic *Escherichia coli*. Front Cell Infect Microbiol. 2017; 6:200. doi: 10.3389/fcimb.2016.00200. eCollection;%2016.:200.
18. del Canto F., Botkin D J, Valenzuela P, Popov V, Ruiz-Perez F, Nataro J P, et al. Identification of *Coli*

18. Surface Antigen 23, a novel adhesin of enterotoxigenic *Escherichia coli*. Infect Immun. 2012; 80(8):2791-801.
19. von Mentzer A, Tobias J, Wiklund G, Nordqvist S, Aslett M, Dougan G, et al. Identification and characterization of the novel colonization factor CS30 based on whole genome sequencing in enterotoxigenic *Escherichia coli* (ETEC). Sci Rep. 2017; 7(1):12514-743.
20. Levine M M, Kotloff K L, Nataro J P, Muhsen K. The Global Enteric Multicenter Study (GEMS): Impetus, Rationale, and Genesis. Clin Infect Dis. 2012; 55 Suppl 4:S215-24. doi: 10.1093/cid/cis761.:S215-S224.
21. Farag T H, Nasrin D, Wu Y, Muhsen K, Blackwelder W C, Sommerfelt H, et al. Some Epidemiologic, Clinical, Microbiologic, and Organizational Assumptions That Influenced the Design and Performance of the Global Enteric Multicenter Study (GEMS). Clin Infect Dis. 2012; 55 Suppl 4:S225-31. doi: 10.1093/cid/cis787.:S225-S231.
22. Panchalingam S, Antonio M, Hossain A, Mandomando I, Ochieng B, Oundo J, et al. Diagnostic Microbiologic Methods in the GEMS-1 Case/Control Study. Clin Infect Dis. 2012; 55 Suppl 4:S294-302. doi: 10.1093/cid/cis754.:S294-S302.
23. Kotloff K L, Blackwelder W C, Nasrin D, Nataro J P, Farag T H, van E A, et al. The Global Enteric Multicenter Study (GEMS) of Diarrheal Disease in Infants and Young Children in Developing Countries: Epidemiologic and Clinical Methods of the Case/Control Study. Clin Infect Dis. 2012; 55 Suppl 4:S232-45. doi: 10.1093/cid/cis753.:S232-S245.
24. Vidal R, Vidal M, Lagos R, Levine M, Prado V. Multiplex PCR for diagnosis of enteric infections associated with diarrheagenic *Escherichia coli*. J Clin Microbiol. 2004; 42(4):1787-9.
25. Rodas C, Iniguez V, Qadri F, Wiklund G, Svennerholm A M, Sjoling A. Development of multiplex PCR assays for detection of enterotoxigenic *Escherichia coli* colonization factors and toxins. J Clin Microbiol. 2009; 47(4): 1218-20.
26. Vidal R M, Valenzuela P, Baker K, Lagos R, Esparza M, Livio S, et al. Characterization of the most prevalent colonization factor antigens present in Chilean clinical enterotoxigenic *Escherichia coli* strains using a new multiplex polymerase chain reaction. Diagn Microbiol Infect Dis. 2009; 65(3):217-23.
27. Sjoling A, Wiklund G, Savarino S J, Cohen D I, Svennerholm A M. Comparative analyses of phenotypic and genotypic methods for detection of enterotoxigenic *Escherichia coli* toxins and colonization factors. J Clin Microbiol. 2007; 45(10):3295-301.
28. Pichel M G, Binsztein N, Qadri F, Giron J A. Type IV longus pilus of enterotoxigenic *Escherichia coli*: occurrence and association with toxin types and colonization factors among strains isolated in Argentina. J Clin Microbiol. 2002; 40(2):694-7.
29. McKenzie R, Porter C K, Cantrell J A, Denearing B, O'Dowd A, Grahek S L, et al. Volunteer challenge with enterotoxigenic *Escherichia coli* that express intestinal colonization factor fimbriae CS17 and CS19. J Infect Dis. 2011; 204(1):60-4.
30. Qadri F, Svennerholm A M, Faruque A S, Sack R B. Enterotoxigenic *Escherichia coli* in developing countries: epidemiology, microbiology, clinical features, treatment, and prevention. Clin Microbiol Rev. 2005; 18(3):465-83.
31. Gonzales L, Sanchez S, Zambrana S, Iniguez V, Wiklund G, Svennerholm A M, et al. Molecular characterization of enterotoxigenic *Escherichia coli* isolates recovered from children with diarrhea during a 4-year period (2007 to 2010) in Bolivia. J Clin Microbiol. 2013; 51(4):1219-25.
32. Tacket C O, Maneval D R, Levine M M. Purification, morphology, and genetics of a new fimbrial putative colonization factor of enterotoxigenic *Escherichia coli* 0159:H4. Infect Immun. 1987; 55:1063-9.
33. Giron J A, Levine M M, Kaper J B. Longus: a long pilus ultrastructure produced by human enterotoxigenic *Escherichia coli*. Mol Microbiol. 1994; 12(1):71-82.
34. Giron J A, Viboud G I, Sperandio V, Gomez-Duarte O G, Maneval D R, Albert M J, et al. Prevalence and association of the longus pilus structural gene (lngA) with colonization factor antigens, enterotoxin types, and serotypes of enterotoxigenic *Escherichia coli*. Infect Immun. 1995; 63:4195-8.
35. Guevara C P, Luiz W B, Sierra A, Cruz C, Qadri F, Kaushik R S, et al. Enterotoxigenic *Escherichia coli* CS21 pilus contributes to adhesion to intestinal cells and to pathogenesis under in vivo conditions. Microbiology. 2013; 159(Pt 8):1725-35.
36. Nuccio S P, Baumler A J. Evolution of the chaperone/usher assembly pathway: fimbrial classification goes Greek. Microbiol Mol Biol Rev. 2007; 71(4):551-75.
37. Madhavan T P, Sakellaris H. Colonization factors of enterotoxigenic *Escherichia coli*. Adv Appl Microbiol. 2015; 90:155-97. doi: 10.1016/bs.aambs.2014.09.003. Epub;%2014 Nov. 12.:155-97.
38. Isidean S D, Riddle M S, Savarino S J, Porter C K. A systematic review of ETEC epidemiology focusing on colonization factor and toxin expression. Vaccine. 2011; 29(37):6167-78.
39. Blackwelder W C, Biswas K, Wu Y, Kotloff K L, Farag T H, Nasrin D, et al. Statistical Methods in the Global Enteric Multicenter Study (GEMS). Clin Infect Dis. 2012; 55 Suppl 4:S246-53. doi: 10.1093/cid/cis788.:S246-S253.
40. Firth D. Bias reduction of maximum likelihood estimates. Biometrika. 1993; 80:27-38.
41. Rothman K J. No adjustments are needed for multiple comparisons. Epidemiology. 1990; 1(1):43-6.
42. Savitz D A, Olshan A F. Multiple comparisons and related issues in the interpretation of epidemiologic data. Am J Epidemiol. 1995; 142(9):904-8.
43. Savitz D A, Olshan A F. Describing data requires no adjustment for multiple comparisons: a reply from Savitz and Olshan. Am J Epidemiol. 1998; 147(9):813-4.
44. Perneger T V. What's wrong with Bonferroni adjustments. BMJ. 1998; 316(7139):1236-8.
45. Evans D J, Jr., Evans D G, DuPont H L, Orskov F, Orskov I. Patterns of loss of enterotoxigenicity by *Escherichia coli* isolated from adults with diarrhea: suggestive evidence for an interrelationship with serotype. Infect Immun. 1977; 17(1):105-11.
46. Tobias J, von MA, Loayza F P, Aslett M, Page A J, Sjoling A, et al. Stability of the Encoding Plasmids and Surface Expression of CS6 Differs in Enterotoxigenic *Escherichia coli* (ETEC) Encoding Different Heat-Stable (ST) Enterotoxins (STh and STp). PLoS ONE. 2016; 11(4):e0152899.
47. Echeverria P, Seriwatana J, Taylor D N, Changchawalit S, Smyth C J, Twohig J, et al. Plasmids coding for colonization factor antigens I and II, heat-labile enterotoxin, and heat-stable enterotoxin A2 in *Escherichia coli*. Infect Immun. 1986; 51(2):626-30.
48. Evans D G, Evans D J, Jr. New surface-associated heat-labile colonization factor antigen (CFA/II) produced by enterotoxigenic *Escherichia coli* of serogroups 06 and 08. Infect Immun. 1978; 21(2):638-47.

49. Liu J, Platts-Mills J A, Juma J, Kabir F, Nkeze J, Okoi C, et al. Use of quantitative molecular diagnostic methods to identify causes of diarrhoea in children: a reanalysis of the GEMS case-control study. Lancet. 2016; 388(10051): 1291-301.
50. Levine M M, Ferreccio C, Prado V, Cayazzo M, Abrego P, Martinez J, et al. Epidemiologic studies of *Escherichia coli* infections in a low socioeconomic level periurban community in Santiago, Chile. Am J Epidemiol. 1993; 138:849-69.
51. Platts-Mills J A, Babji S, Bodhidatta L, Gratz J, Haque R, Havt A, et al. Pathogen-specific burdens of community diarrhoea in developing countries: a multisite birth cohort study (MAL-ED). Lancet Glob Health. 2015; (15):10-109X.
52. Satterwhite T K, Evans D G, DuPont H L, Evans D J, Jr. Role of *Escherichia coli* colonisation factor antigen in acute diarrhoea. Lancet. 1978; 2(8082):181-4.
53. Viboud G I, Jouve M J, Binsztein N, Vergara M, Rivas M, Quiroga M, et al. Prospective cohort study of enterotoxigenic *Escherichia coli* infections in Argentinean children. J Clin Microbiol. 1999; 37(9):2829-33.
54. Lumish R M, Ryder R W, Anderson D C, Wells J G, Puhr N D. Heat-labile enterotoxigenic *Escherichia coli* induced diarrhea aboard a Miami-based cruise ship. Am J Epidemiol. 1980; 111(4):432-6.
55. Levine M M, Nalin D R, Hoover D L, Bergquist E J, Hornick R B, Young C R. Immunity to enterotoxigenic *Escherichia coli*. Infect Immun. 1979; 23:729-36.
56. Leach S, Lundgren A, Carlin N, Lofstrand M, Svennerholm A M. Cross-reactivity and avidity of antibody responses induced in humans by the oral inactivated multivalent enterotoxigenic *Escherichia coli* (ETEC) vaccine ETVAX. Vaccine. 2017; (17):10.
57. Barry E M, Wang J, Wu T, Davis T, Levine M M. Immunogenicity of multivalent *Shigella*-ETEC candidate vaccine strains in a guinea pig model. Vaccine. 2006; 24(18):3727-34.
58. Anantha R P, McVeigh A L, Lee L H, Agnew M K, Cassels F J, Scott D A, et al. Evolutionary and functional relationships of colonization factor antigen i and other class 5 adhesive fimbriae of enterotoxigenic *Escherichia coli*. Infect Immun. 2004; 72(12):7190-201.
59. Gaastra W, Sommerfelt H, van DL, Kusters J G, Svennerholm A M, Grewal H M. Antigenic variation within the subunit protein of members of the colonization factor antigen I group of fimbrial proteins in human enterotoxigenic *Escherichia coli*. Int J Med Microbiol. 2002; 292(1):43-50.
60. Fleckenstein J, Sheikh A, Qadri F. Novel antigens for enterotoxigenic *Escherichia coli* vaccines. Expert Rev Vaccines. 2014; 13(5):631-9.
61. Caron J, Scott J. A ms-like regulator gene in CFA/I that controls expression of CFA/I pilin. Infect Immun. 1990; 58:874-8.
62. Caron J, Coffield L M, Scott J R. A plasmid-encoded regulatory gene, rns, required for expression of the CS1 and CS2 adhesins of enterotoxigenic *Escherichia-coli*. Proc Natl Acad Sci USA. 1989; 86:963-7.
63. Bodero M D, Munson G P. The Virulence Regulator Rns Activates the Expression of CS14 Pili. Genes (Basel). 2016; 7(12):genes7120120.
64. Haines S, Gautheron S, Nasser W, Renauld-Mongenie G. Identification of Novel Components Influencing Colonization Factor Antigen I Expression in Enterotoxigenic *Escherichia coli*. PLoS ONE. 2015; 10(10):e0141469.
65. Haines S, Arnaud-Barbe N, Poncet D, Reverchon S, Wawrzyniak J, Nasser W, et al. IscR Regulates Synthesis of Colonization Factor Antigen I Fimbriae in Response to Iron Starvation in Enterotoxigenic *Escherichia coli*. J Bacteriol. 2015; 197(18):2896-907.
66. Hodson C, Yang J, Hocking D M, Azzopardi K, Chen Q, Holien J K, et al. Control of Virulence Gene Expression by the Master Regulator, CfaD, in the Prototypical Enterotoxigenic *Escherichia coli* Strain, H10407. Front Microbiol. 2017; 8:1525. doi: 10.3389/fmicb.2017.01525. eCollection;%2017.:1525.
67. Wolf M K, Andrews G P, Tall B D, McConnell M M, Levine M M, Boedeker E C. Characterization of CS4 and CS6 antigenic components of PCF8775, a putative colonization factor complex from enterotoxigenic *Escherichia coli* E8775. Infect Immun. 1989; 57:164-73.
68. Caron J, Maneval D R, Kaper J B, Scott J R. Association of RNs Homologs with Colonization Factor Antigens in Clinical *Escherichia-Coli* Isolates. Infect Immun. 1990; 58:3442-4.
69. Favre D, Ludi S, Stoffel M, Frey J, Horn M P, Dietrich G, et al. Expression of enterotoxigenic *Escherichia coli* colonization factors in *Vibrio cholerae*. Vaccine. 2006; 24(20):4354-68.
70. Nicklasson M, Sjoling A, von MA, Qadri F, Svennerholm A M. Expression of colonization factor CS5 of enterotoxigenic *Escherichia coli* (ETEC) is enhanced in vivo and by the bile component Na glycocholate hydrate. PLoS ONE. 2012; 7(4):e35827.
71. Nicklasson M, Sjoling A, Lebens M, Tobias J, Janzon A, Brive L, et al. Mutations in the periplasmic chaperone leading to loss of surface expression of the colonization factor CS6 in enterotoxigenic *Escherichia coli* (ETEC) clinical isolates. Microb Pathog. 2008; 44(3):246-54.
72. Darsley M J, Chakraborty S, Denearing B, Sack D A, Feller A, Buchwaldt C et al. The oral, live attenuated enterotoxigenic *Escherichia coli* vaccine ACE527 reduces the incidence and severity of diarrhea in a human challenge model of diarrheal disease. *Clin. Vaccine Immunol.* 2012; 19:1921-31.
73. Levine M M, Ferreccio C, Prado V, Cayazzo M, Abrego P, Martinez J et al. Epidemiologic studies of *Escherichia coli* infections in a low socioeconomic level periurban community in Santiago, Chile. *Am. J. Epidemiol.* 1993; 138:849-69.
74. von Mentzer A, Connor T R, Wieler L H, Semmler T, Iguchi A, Thomson N R et al. Identification of enterotoxigenic *Escherichia coli* (ETEC) clades with long-term global distribution. *Nat. Genet.* 2014; 46:1321-6.
75. Wu et al., Infect. Immun. 79(12):4912-4922, 2011 PMC3232646.
76. Delaine et al., Pathog. Dis. 74(5), 2016 PMC5985478.
77. Datsenko and Wanner, Proc. Natl. Acad. Sci. 97(12): 6640-6645, 2000.

The invention claimed is:

1. A vaccine composition for prophylaxis of diarrheal disease due to *Shigella flexneri* and enterotoxigenic *Escherischia coli* (ETEC), comprising:
   a) a live attenuated *Shigella* strain selected from the group consisting of *Shigella flexneri* serotype 7a, *Shigella flexneri* serotype 1b, and both *Shigella flexneri* serotype 7a and *Shigella flexneri* serotype 1b;
   b) enterotoxigenic *Escherischia coli* surface antigen CS14, wherein the ETEC CS14 is expressed in one or both of the live attenuated *Shigella* strains.

2. The vaccine composition of claim 1, further comprising one or more of:
   c) a live attenuated strain of *Shigella sonnei*;
   d) a live attenuated strain of *Shigella flexneri* serotype 2a;
   e) a live attenuated strain of *Shigella flexneri* serotype 3a; and
   f) a live attenuated strain of *Shigella flexneri* serotype 6.

3. The vaccine composition of claim 1, further comprising:
   c) a live attenuated strain of *Shigella sonnei*;
   d) a live attenuated strain of *Shigella flexneri* serotype 2a;
   e) a live attenuated strain of *Shigella flexneri* serotype 3a; and
   f) a live attenuated strain of *Shigella flexneri* serotype 6.

4. The vaccine composition of claim 2, further comprising an attenuated strain of *Shigella dysenteriae*.

5. The vaccine composition of claim 3, further comprising an attenuated strain of *Shigella dysenteriae*.

6. The vaccine composition of claim 2, wherein one or more of the live attenuated *Shigella flexneri* strains *Shigella flexneri* serotype 2a, *Shigella flexneri* serotype 3a, and *Shigella flexneri* serotype 6 is engineered to express one or more enterotoxigenic *Escherichia coli* (ETEC) antigens.

7. The vaccine composition of claim 3, wherein one or more of the live attenuated *Shigella flexneri* strains *Shigella flexneri* serotype 2a, *Shigella flexneri* serotype 3a, and *Shigella flexneri* serotype 6 is engineered to express one or more enterotoxigenic *Escherichia coli* (ETEC) antigens.

8. The vaccine composition of claim 1, which further comprises one or more ETEC antigens selected from the group consisting of *Coli* Surface antigens (CS)1, CS2, CS3, CS4, CS5, CS6, Colonization Factor Antigen 1 (CFA/1), eltB (LTB), a tip adhesin, and Shiga toxin B (StxB), wherein the ETEC antigens are expressed in one or both of the live attenuated *Shigella* strains.

9. The vaccine composition of claim 1, further comprising a pharmaceutically acceptable carrier.

10. The vaccine composition of claim 2, further comprising a pharmaceutically acceptable carrier.

11. The vaccine composition of claim 3, further comprising a pharmaceutically acceptable carrier.

12. The vaccine composition of claim 3, wherein the *Shigella* strains contain mutations in guaBA and sen.

13. The vaccine composition of claim 3, comprising:
   a) live attenuated *S. sonnei*, strain CVD 1233S, which expresses ETEC antigens CS2 and CS3;
   b) live attenuated *S. flexneri* serotype 2a, strain CVD 1208S, which expresses ETEC antigens CFA/1 and LTB;
   c) live attenuated *S. flexneri* serotype 3a, strain CVD 1213, which expresses ETEC antigens CS1 and CS5;
   d) live attenuated *S. flexneri* serotype 6, strain CVD 1215, which expresses ETEC antigens CS4 and CS6;
   e) live attenuated *S. flexneri* serotype 1b, strain CVD 1224, which expresses ETEC antigen CS14; and
   f) live attenuated *S. flexneri* serotype 7a, strain CVD 1242, which expresses one or more ETEC tip adhesin antigens.

14. The vaccine composition of claim 13, further comprising live attenuated *S. dysenteriae*, strain CVD 1254, which expresses ETEC antigens CFA/1 and LTB.

15. A method of vaccinating a subject in need thereof against diarrheal disease due to *Shigella flexneri* or enterotoxigenic *Escherischia coli*, comprising administering the composition of claim 1 to the subject.

16. A method of vaccinating a subject in need thereof against diarrheal disease due to *Shigella flexneri* or enterotoxigenic *Escherischia coli*, comprising administering the composition of claim 3 to the subject.

17. The method of claim 15, wherein the subject resides in an area where diarrheal disease is endemic.

18. The method of claim 16 wherein the subject resides in an area where diarrheal disease is endemic.

19. The method of claim 15 wherein the subject is a child of less than 5 years old.

20. The method of claim 16 wherein the subject is a child of less than 5 years old.

* * * * *